(12) United States Patent
Provins et al.

(10) Patent No.: US 7,544,675 B2
(45) Date of Patent: Jun. 9, 2009

(54) CHEMICAL COMPOUNDS WITH DUAL ACTIVITY, PROCESSES FOR THEIR PREPARATION AND PHARMACEUTICAL COMPOSITIONS

(75) Inventors: Laurent Provins, Soignies (BE); Berend Jan Van Keulen, Tubize (BE); John Surtees, Jezus-Eik (BE); Patrice Talaga, Watermael-Boitsfort (BE); Bernard Christophe, Ramillies (BE)

(73) Assignee: UCB, S.A., Brussels (BE)

( * ) Notice: Subject to any disclaimer, the term of this patent is extended or adjusted under 35 U.S.C. 154(b) by 483 days.

(21) Appl. No.: 10/511,660

(22) PCT Filed: Mar. 29, 2003

(86) PCT No.: PCT/EP03/03299

§ 371 (c)(1), (2), (4) Date: Oct. 5, 2005

(87) PCT Pub. No.: WO03/087064

PCT Pub. Date: Oct. 23, 2003

(65) Prior Publication Data

US 2006/0074068 A1    Apr. 6, 2006

(30) Foreign Application Priority Data

Apr. 18, 2002    (EP) .................................. 02008706

(51) Int. Cl.
*C07D 239/48*    (2006.01)
*C07D 239/42*    (2006.01)
*A61K 31/505*   (2006.01)

(52) U.S. Cl. ................ 514/183; 514/217.06; 514/227.8; 514/256; 540/481; 540/601; 544/60; 544/326

(58) Field of Classification Search ................. 540/481, 540/601; 544/60, 326; 514/183, 217.06, 514/227.8, 256
See application file for complete search history.

(56) References Cited

U.S. PATENT DOCUMENTS 3,624,084 A * 11/1971 Mathieu ...................... 544/326

FOREIGN PATENT DOCUMENTS

| EP | 0 256 670 A | 2/1988 |
| EP | 0 300 726 A | 1/1989 |

OTHER PUBLICATIONS

Barnes, Frontrunners in novel pharmacotherapy of COPD, Current Opinion in Pharmacology 2008, 8:300-307.*
Cazzola et al., Treating systemic effects of COPD, Trends in Pharmacological Sciences, vol. 28, No. 10, pp. 544-550, 2007.*
Fox et al., Models of chronic obstructive pulmonary disease: a review of current status, Drug Discovery Today: Disease Models, vol. 1, No. 3, pp. 319-328 (2004).*

* cited by examiner

*Primary Examiner*—Deepak Rao
(74) *Attorney, Agent, or Firm*—McDonnell Boehnen Hulbert & Berghoff LLP

(57) ABSTRACT

The present invention concerns chemical compounds combining affinity and antagonism against the human m3 muscarinic receptor with activity as selective phosphodiesterase IV (PDE IV) inhibitors, processes for preparing them, pharmaceutical compositions containing them and their use as pharmaceuticals.

33 Claims, No Drawings

CHEMICAL COMPOUNDS WITH DUAL ACTIVITY, PROCESSES FOR THEIR PREPARATION AND PHARMACEUTICAL COMPOSITIONS

This application is a National Stage of International Application No. PCT/EP03/03299, filed Mar. 29, 2003, which claims priority from European Patent Application No. 02008706.0, filed Apr. 18, 2002.

The present invention concerns chemical compounds combining affinity and antagonism against the human m3 muscarinic receptor with activity as selective phosphodiesterase IV (PDE IV) inhibitors, processes for preparing them, pharmaceutical compositions containing them and their use as pharmaceuticals.

Chronic obstructive pulmonary disease is characterised by airway inflammation and impaired expiratory outflow due to chronic bronchitis and/or emphysema. The primary inflammatory cells associated with COPD are macrophages, CD8+ T-cells and neutrophils.

Parasympathetic cholinergic reflexes are the most potent tonically active regulators of bronchoconstriction and of submucosal gland exocytosis and secretion in the airways. Postjunctional m3 receptors mediate cholinergic bronchoconstriction and glandular secretion in the human airways. Prejunctional m2 autoreceptors modulate the acetylcholine release whereas m1 receptors located on parasympathetic ganglia inversely facilitate the parasympathetic nerve activity (Barnes P. J., In: "Lung Biology in Health and Disease: Anticholinergic Agents in the Upper and Lower Airways", Vol. 134, Spector S. L. (Ed), (1999), 31-57).

The nasal mucosa of the upper airway is also innervated by parasympathetic nerve fibers, activation of which results in glandular hypersecretion from both goblet cells and submucosal seromucinous glands. Activation of m1 and m3 receptors results in secretion from mucous and serous glands. The m3 receptor subtype, also present on blood vessels, may play an additional role in nasal congestion through promoting vasodilatation.

Thereby, $M_3$ and $M_1$ muscarinic receptor antagonists are indicated for the treatment of diseases associated with airway narrowing or/and mucus hypersecretion (Morley, J. Parasympatholytics in Asthma. Pulmonary Pharmacology (1994), 7, 159-168).

Anticholinergic bronchodilators, particularly selective muscarinic $M_3$ antagonists, are currently the preferred choice for management of COPD as they are more effective and have fewer side effects compared to $\beta_2$-adrenoceptor agonists. Bronchodilators improve symptoms but do not address the underlying chronic inflammation or the changes in airway structure (Hay D. W. P., Current Opinion in Chemical Biology (2000), 4, 412-419).

Amongst phosphodiesterases, PDE IV is the predominant sub-type in inflammatory cells, including mast cells, eosinophils, T lymphocytes, neutrophils and macrophages. It is also the dominant sub-type in structural cells such as sensory nerves and epithelial cells (Torphy T. J., Am. J. Resp. Crit. Care Med. (1998), 157, 351-370).

Standard treatment with corticosteroids as anti-inflammatory agents has demonstrated limited efficacy (Culpitt S. V., Maziak W., Loukidis S., Nightingale J. A., Matthews J. L., Barnes P. J., Am. J. Resp. Crit. Care Med. (1999), 160, 1635-9); Keatings V. M., Jatakanon A., Wordsell Y. M., Barnes P. J., Am. J. Resp. Crit. Care Med. (1997), 155, 542-8). Selective PDE IV inhibitors, however, have proved to be very efficient in attenuating the responses of various inflammatory cells through their ability to elevate cyclic AMP levels. They are known to modulate activity, migration and apoptosis of neutrophils by inhibiting the production and release of chemokines, superoxide free radicals, leukotrienes and proteolytic and toxic granular enzymes (Torphy T. J., Am. J. Resp. Crit. Care Med. (1998), 157, 351-370).

It has now been found that a combination of these two therapeutic activities, bronchodilatation with an $M_3$ muscarinic antagonist and anti-inflammatory activity with a selective PDE IV inhibitor, in a single compound, provides a new and surprisingly effective approach to the treatment of COPD.

The compounds according to this invention are useful for treating respiratory disorders in connection with Chronic Obstructive Pulmonary Disease (COPD).

Preferred compounds have affinity for the human m3 muscarinic receptor at concentrations ranging from 100 nM to almost 1 nM and incorporate activity as selective phosphodiesterase IV (PDE IV) inhibitors at concentrations ranging from 2.5 µM to almost 50 nM. These compounds also recognize the m1, m2, m4 and m5 receptors with variable receptor subtype selectivity.

Preferred compounds have been proven to antagonise carbachol-induced contraction of guinea-pig trachea in vitro.

In one aspect, the invention therefore provide compounds having the formula I, or a pharmaceutically acceptable salt thereof,

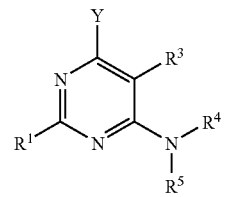

(I)

wherein
Y is —NH—$R^2$ or a group of formula

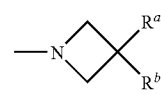

$R^1$ is cycloalkyl or non-substituted alkyl,
$R^2$ is cycloalkyl,
$R^3$ is hydrogen, alkyl, halogen, hydroxy, alkoxy or amino,
or $R^2R^3$ is an alkylene bridging group,
$R^a$ is hydrogen, alkyl, alkenyl, alkynyl, halogen, hydroxy, alkoxy, amino, alkylamino, alkylsulfonyloxy, cyano, carboxy, ester or amido,
$R^b$ is hydrogen, alkyl or halogen,
or $R^aR^b$ is carbonyl,
$R^4$ is hydrogen or alkyl,
$R^5$ is cycloalkyl, arylalkyl or heterocycle-alkyl,
or $NR^4R^5$ is a heterocycle, which may be substituted, containing only one heteroatom which is a nitrogen atom or containing two heteroatoms wherein one is a nitrogen atom and the other is a non-oxidized sulfur atom, with the proviso that when Y is —NHR² and R²R³ is an alkylene bridging group or when Y is a group of formula

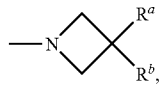

R¹ is a cycloalkyl.

Compounds wherein Y is —NHR² are named compounds Ia.

Compounds wherein Y represents a group of formula

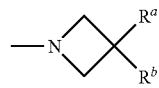

are named compounds Ib.

The term "alkyl", as used herein, is defined as including saturated, monovalent hydrocarbon radicals having straight, branched or cyclic moieties or combinations thereof and containing 1-20 carbon atoms, preferably 1-6 carbon atoms for non-cyclic alkyl and 3-8 carbon atoms for cycloalkyl (in these two preferred cases, unless otherwise specified, "lower alkyl") and includes alkyl moieties substituted by 1 to 5 substituents independently selected from the group consisting of halogen, hydroxy, thiol, amino, nitro, cyano, acyl derivative, sulfonyl derivative, sulfinyl derivative, alkylamino, carboxy, ester, ether, amido, azido, cycloalkyl, sulfonic acid, sulfonamide, thio derivative, esteroxy, amidooxy, heterocycle, vinyl, C1-6-alkoxy, C6-10-aryloxy, C6-10-aryl and oxo. "Non-substituted akyl" represents saturated, monovalent hydrocarbon radicals having straight, branched or cyclic moieties or combinations thereof and containing 1-20 carbon atoms, preferably 1-6 carbon atoms for non-cyclic alkyl and 3-8 carbon atoms for cycloalkyl (in these two preferred cases, unless otherwise specified, "lower alkyl").

Preferred alkyl groups are methyl, ethyl, propyl, isopropyl, butyl, iso- or tert-butyl, and 2,2-dimethylpropyl.

The term "cycloalkyl", as used herein, refers to a monovalent group of 3 to 18 carbons derived from a saturated cyclic or polycyclic hydrocarbon such as adamantyl, which may optionally be substituted with any suitable group, including but not limited to one or more moieties selected from lower alkyl or C6-10-aryl. Non-limiting examples are cyclopropyl, cyclobutyl, cyclopentyl, cyclohexyl, cycloheptyl, cyclooctyl, bicyclo[3.2.1]octyl or adamantyl.

The term "alkenyl" as used herein, is defined as including branched, unbranched and cyclic unsaturated hydrocarbon radicals having at least one double bond and being optionally substituted with any suitable group, including but not limited to one or more moieties selected from lower alkyl or other groups as described above for the alkyl groups. Usually "alkenyl" represents branched, unbranched and cyclic unsaturated hydrocarbon radicals having at least one double bond such as ethenyl (=vinyl), 1-methyl-1-ethenyl, 2-methyl-1-propenyl, 1-propenyl, 2-propenyl (=allyl), 1-butenyl, 2-butenyl, 3-butenyl, 4-pentenyl, 1-methyl-4-pentenyl, 3-methyl-1-pentenyl, 1-hexenyl, 2-hexenyl, and the like.

The term "alkynyl" as used herein, is defined as including a branched, unbranched and cyclic hydrocarbon radical containing at least one carbon-carbon triple bond and being optionally substituted by any suitable group, including but not limited to one or more moieties selected from lower alkyl or other groups as described above for the alkyl groups. Usually "alkynyl" represents branched, unbranched and cyclic hydrocarbon radical containing at least one carbon-carbon triple bond such as ethynyl, 2-propynyl (=propargyl), and the like.

The term "alkylene" as used herein, is defined as including branched, unbranched and cyclic divalent hydrocarbon radicals containing 1-12 carbon atoms, preferably 1-4 carbon atoms, being optionally substituted with any suitable group, including but not limited to one or more moieties selected from lower alkyl or other groups as described above for the allyl groups.

When present as bridging groups, alkyl represents straight or branched chains, C1-12-, preferably C1-4-alkylene.

Groups where branched derivatives are conventionally qualified by prefixes such as "n", "sec", "iso" and the like (e.g. "n-propyl", "sec-butyl") are in the n-form unless otherwise stated.

The term "halogen", as used herein, includes an atom of Cl, Br, F, I.

The term "hydroxy", as used herein, represents a group of the formula —OH.

The term "amino", as used herein, represents a group of the formula —NH₂.

The term "thiol", as used herein, represents a group of the formula —SH.

The term "cyano", as used herein, represents a group of the formula —CN.

The term "nitro", as used herein, represents a group of the formula —NO₂.

The term "alkoxy", as used herein, is defined as including —O—R⁶ groups wherein R⁶ represents an alkyl or a cycloalkyl group. Non-limiting examples are methoxy and ethoxy.

The term "arylalkyl", as used herein, represents a group of the formula —R⁷-aryl in which R⁷ is C1-12-straight, branched or cyclic alkylene. Non-limiting examples are benzyl, halobenzyl, cyanobenzyl, methoxybenzyl, nitrobenzyl, 2-phenylethyl, diphenylmethyl, (4-methoxyphenyl)diphenylmethyl and anthracenylmethyl.

The term "aryl" as used herein, is defined as including an organic radical derived from an aromatic hydrocarbon consisting of 1-3 rings and containing 6-30 carbon atoms by removal of one hydrogen, such as phenyl and naphthyl each optionally substituted by 1 to 5 substituents independently selected from halogen, hydroxy, thiol, amino, nitro, cyano, C1-6-alkoxy, C1-6-alkylthio, C1-6-alkyl, C1-6-haloalkyl. Aryl radicals are preferably monocyclic containing 6-10 carbon atoms. Preferred aryl groups are phenyl and naphthyl each optionally substituted by 1 to 5 substituents independently selected from halogen, nitro, amino, azido, C1-6-alkoxy, C1-6-alkylthio, C1-6-alkyl and C1-6-haloalkyl.

The term "alkylthio", as used herein, is defined as including —S—R⁶ᵃ groups wherein R⁶ᵃ represents an alkyl or a cycloalkyl group. Non-limiting examples are methylthio, ethylthio, propylthio and butylthio.

The term "heterocycle", as used herein is defined as including an aromatic or non aromatic cyclic alkyl, alkenyl, or alkynyl moiety as defined above, having at least one O, S and/or N atom interrupting the carbocyclic ring structure and optionally, one of the carbon of the carbocyclic ring structure may be replaced by a carbonyl. Non-limiting examples of aromatic heterocycles are pyridyl, furyl, pyrrolyl, thienyl, isothiazolyl, imidazolyl, benzimidazolyl, tetrazolyl, quinazolinyl, quinolizinyl, naphthyridinyl, pyridazinyl, pyrimidinyl, pyrazinyl, quinolyl, isoquinolyl, isobenzofuranyl, benzothienyl, pyrazolyl, indolyl, indolizinyl, purinyl, isoindolyl, carbazolyl, thiazolyl, 1,2,4-thiadiazolyl, thieno(2,3-b) furanyl, furopyranyl, benzofuranyl, benzoxepinyl, isooxazolyl, oxazolyl, thianthrenyl, benzothiazolyl, or benzoxazolyl, cinnolinyl, phthalazinyl, quinoxalinyl, phenanthridinyl, acridinyl, perimidinyl, phenanthrolinyl, phenothiazinyl, furazanyl, isochromanyl, indolinyl, xanthenyl, hypoxanthinyl, pteridinyl, 5-azacytidinyl, 5-azauracilyl, triazolopyridinyl, imidazolopyridinyl, pyrrolopyrimidinyl, and pyrazolopyrimidinyl optionally substituted by alkyl or as described above for the alkyl groups. Non-limiting examples of non aromatic heterocycles are tetrahydrofuranyl, tetrahydropyranyl, piperidinyl, piperidyl, piperazinyl, imidazolidinyl, morpholino, morpholinyl, 1-oxaspiro(4.5)dec-2-yl, pyrrolidinyl, 2-oxo-pyrrolidinyl, 8-thia bicyclo[3.2.1] cyclooctanyl, 1,4-dithiepanyl, tetrahydro-2H-thiopyranyl, azepanyl, azocanyl, or the same which can optionally be substituted with any suitable group, including but not limited to one or more moieties selected from lower alkyl, alkylidene or other groups as described above for the alkyl groups. The term "heterocycle" also includes bicyclic, tricyclic and tetracyclic, spiro groups in which any of the above heterocyclic rings is fused to one or two rings independently selected from an aryl ring, a cycloalkyl ring, a cycloalkenyl ring or another monocyclic heterocyclic ring or where a monocyclic heterocyclic group is bridged by an alkylene group, such as quinuclidinyl, 7-azabicyclo(2.2.1)heptanyl, 7-oxabicyclo(2.2.1) heptanyl, 8-azabicyclo(3.2.1)octanyl.

The term "heterocycle-alkyl", as used herein, represents a group of the formula —$R^7$-heterocycle in which $R^7$ is C1-12- straight, branched or cyclic alkylene. Non-limiting examples are thiophenemethyl, thiophenethyl, pyridylmethyl and pyridylethyl.

The term "amido", as used herein, is defined as including a group of formula —$CONR^8R^9$ wherein $R^8$ and $R^9$ are the same or different and each is independently a hydrogen, alkyl or aryl group as defined above.

The term "alkylamino", as used herein, is defined as including a group of formula —$NR^{10}R^{11}$ wherein $R^{10}$ and $R^{11}$ are the same or different and each is independently hydrogen or an alkyl group as defined above, with the proviso that at least one of $R^{10}$ and $R^{11}$ is not hydrogen.

The term "pharmaceutically acceptable salt" according to the invention includes therapeutically active, non-toxic base and acid salt forms which the compounds of formula I are able to form.

The acid addition salt form of a compound of formula I that occurs in its free form as a base can be obtained by treating the free base with an appropriate acid such as an inorganic acid, for example, a hydrohalic such as hydrochloric or hydrobromic, sulfuric, nitric, phosphoric and the like; or an organic acid, such as, for example, acetic, hydroxyacetic, propanoic, lactic, pyruvic, malonic, succinic, maleic, fumaric, malic, tartaric, citric, methanesulfonic, ethanesulfonic, benzenesulfonic, p-toluenesulfonic, cyclamic, salicylic, p-aminosalicylic, pamoic and the like.

The compounds of formula I containing acidic protons may be converted into their therapeutically active, non-toxic base addition salt forms, e.g. metal or amine salts, by treatment with appropriate organic and inorganic bases. Appropriate base salt forms include, for example, ammonium salts, alkali and earth alkaline metal salts, e.g. lithium, sodium, potassium, magnesium, calcium salts and the like, salts with organic bases, e.g. N-methyl-D-glucamine, hydrabamine salts, and salts with amino acids such as, for example, arginine, lysine and the like.

Conversely said salt forms can be converted into the free forms by treatment with an appropriate base or acid.

Compounds of the formula I and their salts can be in the form of a solvate, which is included within the scope of the present invention. Such solvates include for example hydrates, alcoholates and the like.

Some of the compounds of formula I and some of their intermediates have at least one stereogenic center in their structure. This stereogenic center may be present in a R or a S configuration, said R and S notation is used in correspondence with the rules described in Pure Appl. Chem., 45 (1976) 11-30.

The invention also relates to all stereoisomeric forms such as enantiomeric and diastereomeric forms of the compounds of formula I or mixtures thereof (including all possible mixtures of stereoisomers). Reference to a compound or compounds is intended to encompass that compound in each of its possible isomeric forms and mixtures thereof unless the particular isomeric form is referred to specifically.

Some of the compounds of formula I may also exist in tautomeric forms. Such forms although not explicity, indicated in the above formula, are intended to be included within the scope of the present invention.

The invention also includes within its scope pro-drug forms of the compounds of formula I and its various subscopes and sub-groups.

The term "prodrug" as used herein includes compound forms which are rapidly transformed in vivo to the parent compound according to the invention, for example, by hydrolysis in blood. Prodrugs are compounds bearing groups which are removed by biotransformation prior to exhibiting their pharmacological action. Such groups include moieties which are readily cleaved in vivo from the compound bearing it, which compound after cleavage remains or becomes pharmacologically active. Metabolically cleavable groups form a class of groups well known to practitioners of the art. They include, but are not limited to such groups as alkanoyl (i.e. acetyl, propionyl, butyryl, and the like), unsubstituted and substituted carbocyclic aroyl (such as benzoyl, substituted benzoyl and 1- and 2-naphthoyl), alkoxycarbonyl (such as ethoxycarbonyl), trialkylsilyl (such as trimethyl- and triethylsilyl), monoesters formed with dicarboxylic acids (such as succinyl), phosphate, sulfate, sulfonate, sulfonyl, sulfinyl and the like. The compounds bearing the metabolically cleavable groups have the advantage that they may exhibit improved bioavailability as a result of enhanced solubility and/or rate of absorption conferred upon the parent compound by virtue of the presence of the metabolically cleavable group. T. Higuchi and V. Stella, "Pro-drugs as Novel Delivery System", Vol. 14 of the A.C.S. Symposium Series; "Bioreversible Carriers in Drug Design", ed. Edward B. Roche, American Pharmaceutical Association and Pergamon Press, 1987.

According to a first embodiment of the invention compounds are compounds of formula Ia

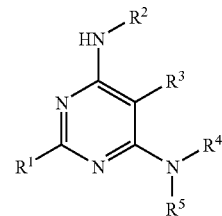

(Ia)

or a pharmaceutically acceptable salt thereof wherein $R^1$, $R^2$, $R^3$, $R^4$ and $R^5$ are as defined above.

Usually, $R^1$ is C3-7-cycloalkyl or non-substituted alkyl.

Usually, $R^2$ is C3-7-cycloalkyl, $R^3$ being as defined above, or $R^2R^3$ is a C2-4 alkylene bridging group.

Usually, $R^3$ is hydrogen, C1-4-alkyl, halogen, hydroxy, alkoxy or amino, $R^2$ being as defined above, or $R^2R^3$ is a C2-4 alkylene bridging group.

Usually, $R^4$ is hydrogen or C1-4-alkyl, $R^5$ being as defined above, or $NR^4R^5$ is a heterocycle, which may be substituted, containing only one heteroatom which is a nitrogen atom or containing two heteroatoms wherein one is a nitrogen atom and the other is a non-oxidized sulfur atom.

Usually, $R^5$ is C3-7-cycloalkyl, arylalkyl or heterocycle-alkyl, $R^4$ being as defined above, or $NR^4R^5$ is a heterocycle, which may be substituted, containing only one heteroatom which is a nitrogen atom or containing two heteroatoms wherein one is a nitrogen atom and the other is a non-oxidized sulfur atom.

Generally $R^1$ is a non-substituted alkyl, a non-substituted cycloalkyl, a cycloalkyl substituted by a lower alkyl, or an alkyl substituted by a cycloalkyl.

Preferably, $R^1$ is C3-4-alkyl or C3-5-cycloalkyl, more preferably $R^1$ is selected from the group of cyclopropyl, isopropyl, cyclobutyl, cyclopentyl, 2-methyl-cyclopropyl and cyclopropylmethyl.

Generally $R^2$ is a non-substituted cycloalkyl, or a cycloalkyl substituted by a lower alkyl or an aryl.

Preferably, $R^2$ is a non-substituted C3-4-cycloalkyl. More preferably $R^2$ is selected from cyclopropyl or cyclobutyl.

Generally $R^3$ is hydrogen, halogen, amino, non-substituted alkoxy or a non-substituted alkyl.

Preferably, $R^3$ is hydrogen, methyl, ethyl, a Cl atom, a F atom, a Br atom, amino or methoxy.

In other preferred embodiments $R^2R^3$ is an alkylene bridging group selected from ethylene, propylene and butylene.

Generally $R^4$ is hydrogen or a non-substituted alkyl.

Preferably, $R^4$ is hydrogen or C1-4-alkyl. More preferably $R^4$ is hydrogen or methyl.

Preferably, $R^5$ is 2-(2-thienyl)ethyl, 2-furylmethyl, 2-thienylmethyl, 4-pyridinylmethyl, benzyl, 2-(methylsulfanyl)benzyl, 2,6-difluorobenzyl, 2-fluorobenzyl, 2-nitrobenzyl, 3,5-bis(trifluoromethyl)benzyl, 3,5-difluorobenzyl, cyclohexyl, cycloheptyl, 4-methylcyclohexyl, or 2,2-diphenylethyl.

In other preferred embodiments, $NR^4R^5$ is 1,3-thiazolidin-3-yl, 1-azepanyl, 1-azocanyl, 3,5-dimethyl-1-piperidinyl, 4-(2-methoxyphenyl)-1-piperidinyl, 4-(hydroxy(diphenyl)methyl)-1-piperidinyl, 4-(trifluoromethyl)-1-piperidinyl, 4,4-difluoro-1-piperidinyl, 4,4-dimethyl-1-piperidinyl, 4-carbamoyl-1-piperidinyl, 4-benzyl-1-piperidinyl, 4-carboxy-1-piperidinyl, 4-cyano-4-phenyl-1-piperidinyl, 4-ethoxycarbonyl-1-piperidinyl, 4-ethyl-1-piperidinyl, 4-ethyl-4-methyl-1-piperidinyl, 4-hydroxy-1-piperidinyl, 4-hydroxy-4-phenyl-1-piperidinyl, 4-hydroxymethyl-1-piperidinyl, 4-methyl-1-piperidinyl, 4-methylene-1-piperidinyl, 4-oxo-1-piperidinyl, 3,6-dihydro-1(2H)-pyridinyl, 3-azabicyclo[3.2.1]oct-3-yl, 4-thiomorpholinyl, 2-one-1-azepanyl, 3,4-dihydro-2(1H)-isoquinolinyl, 1,4-dioxa-8-azaspiro[4.5]dec-8-yl, 1,3,3-trimethyl-6-azabicyclo[3.2.1]oct-6-yl, octahydro-2(1H)-isoquinolinyl or 8-azaspiro[4.5]dec-8-yl.

Combinations of one or more of these preferred compound groups are especially preferred.

More preferred compounds Ia are:

6-(1-azepanyl)-2-cyclobutyl-N-cyclopropyl-5-methyl-4-pyrimidinamine; 6-(1-azepanyl)-N,2-dicyclopropyl-5-methyl-4-pyrimidinamine; 6-(1-azepanyl)-5-chloro-N,2-dicyclopropyl-4-pyrimidinamine; 6-(1-azepanyl)-N,2-dicyclopropyl-5-fluoro-4-pyrimidinamine; 6-azepan-1-yl-5-bromo-N,2-dicyclopropyl-4-pyrimidinamine; 6-(1-azepanyl)-N,2-dicyclopropyl-4-pyrimidinamine; 6-(1-azepanyl)-$N^4$,2-dicyclopropyl-4,5-pyrimidinediamine; 6-(1-azepanyl)-N-cyclopropyl-2-isopropyl-5-methyl-4-pyrimidinamine; 6-(1-azepanyl)-N-cyclopropyl-5-methyl-2-(2-methylcyclopropyl)-4-pyrimidinamine; 6-(1-azocanyl)-N,2-dicyclopropyl-5-methyl-4-pyrimidinamine; N,2-dicyclopropyl-5-methyl-6-[4-(trifluoromethyl)piperidin-1-yl]-4-pyrimidinamine; N,2-dicyclopropyl-6-(4,4-difluoro-1-piperidinyl)-5-methyl-4-pyrimidinamine; N,2-dicyclopropyl-6-(4,4-dimethyl-1-piperidinyl)-5-methyl-4-pyrimidinamine; N,2-dicyclopropyl-6-(4-ethyl-1-piperidinyl)-5-methyl-4-pyrimidinamine; N,2-dicyclopropyl-5-ethyl-6-(4-methyl-1-piperidinyl)-4-pyrimidinamine; N,2-dicyclopropyl-5-methyl-6-(4-methyl-1-piperidinyl)-4-pyrimidinamine; N-cyclopropyl-5-methyl-2-(2-methylcyclopropyl)-6-(4-methyl-1-piperidinyl)-4-pyrimidinamine; N,2-dicyclopropyl-5-methyl-6-(4-methylene-1-piperidinyl)-4-pyrimidinamine; N,2-dicyclopropyl-6-(3,6-dihydro-1(2H)-pyridinyl)-5-methyl-4-pyrimidinamine; 6-(3-azabicyclo[3.2.1]oct-3-yl)-N,2-dicyclopropyl-5-methyl-4-pyrimidinamine; N,2-dicyclopropyl-5-ethyl-6-(4-thiomorpholinyl)-4-pyrimidinamine; N,2-dicyclopropyl-5-methyl-6-(4-thiomorpholinyl)-4-pyrimidinamine; $N^4$,2-dicyclopropyl-$N^6$-(2,6-difluorobenzyl)-5-methyl-4,6-pyrimidinediamine; $N^4$-cyclohexyl-$N^6$-cyclopropyl-2-(2-methylcyclopropyl)-4,6-pyrimidinediamine; $N^4$,2-dicyclopropyl-5-methyl-$N^6$-(4-methylcyclohexyl)-4,6-pyrimidinediamine; 6-(1-azepanyl)-2-cyclopentyl-N-cyclopropyl-5-methyl-4-pyrimidinamine; 4-azepan-1-yl-2-cyclopropyl-5,6,7,8-tetrahydro-pyrido[2,3-d]pyrimidinamine; 4-azepan-1-yl-2-cyclopropyl-6,7,8,9-tetrahydro-pyrimido[4,5-b]azepine; N,2-dicyclopropyl-5-methyl-6-(1-piperidinyl)-4-pyrimidinamine; 6-(3-azabicyclo[3.2.2]non-3-yl)-N,2-dicyclopropyl-5-methyl-4-pyrimidinamine; N,2-dicyclopropyl-5-methyl-6-(2-methyl-1-piperidinyl)-4-pyrimidinamine and N,2-dicyclopropyl-5-methyl-6-(1-pyrrolidinyl)-4-pyrimidinamine, stereoisomeric forms or mixtures thereof, or pharmaceutically acceptable salts thereof.

Most preferred compounds Ia are:

6-(1-azepanyl)-N,2-dicyclopropyl-5-methyl-4-pyrimidinamine; N,2-dicyclopropyl-6-(4,4-dimethyl-1-piperidinyl)-5-methyl-4-pyrimidinamine; N,2-dicyclopropyl-5-methyl-6-(4-methyl-1-piperidinyl)-4-pyrimidinamine; 6-(3-azabicyclo[3.2.1]oct-3-yl)-N,2-dicyclopropyl-5-methyl-4-pyrimidinamine; N,2-dicyclopropyl-5-methyl-6-(4-thiomorpholinyl)-4-pyrimidinamine; 4-azepan-1-yl-2-cyclopropyl-5,6,7,8-tetrahydro-pyrido[2,3-d]pyrimidine and 4-azepan-1-yl-2-cyclopropyl-6,7,8,9-tetrahydro-pyrimido[4,5-b]azepine, or pharmaceutically acceptable salts thereof.

According to another embodiment of the invention, compounds are compounds Ib, or a pharmaceutically acceptable salt thereof,

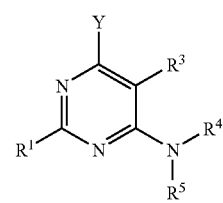

(Ib)

wherein

Y is a group of formula

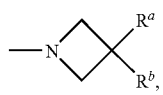

and $R^1$, $R^3$, $R^a$, $R^b$, $R^4$ and $R^5$ are as defined above.

Usually, $R^1$ is C3-7-cycloalkyl.

Usually, $R^3$ is hydrogen, C1-4-alkyl, halogen, hydroxy, alkoxy or amino.

Usually, $R^a$ is hydrogen, C1-4-alkyl, C2-6-alkenyl, C2-6-alkynyl, halogen, hydroxy, alkoxy, amino, alkylamino, alkylsulfonyloxy, cyano, carboxy, ester or amido, $R^b$ being as defined above, or $R^a R^b$ is carbonyl.

Usually, $R^b$ is hydrogen, C1-4-alkyl or halogen, $R^a$ being as defined above, or $R^a R^b$ is carbonyl.

Usually, $NR^4R^5$ is a heterocycle, which may be substituted, containing only one heteroatom which is a nitrogen atom or containing two heteroatoms wherein one is a nitrogen atom and the other is a non-oxidized sulfur atom.

Generally, $R^1$ is a non-substituted C3-7-cycloalkyl, or a C3-7-cycloalkyl substituted by a lower alkyl.

Preferably, $R^1$ is C3-4-cycloalkyl. More preferably, $R^1$ is cyclopropyl.

Generally $R^3$ is hydrogen, halogen, amino, non-substituted alkoxy or a non-substituted C1-4-alkyl.

Preferably, $R^3$ is hydrogen or C1-4-alkyl. More preferably, $R^3$ is hydrogen or methyl.

Generally, $R^a$ is hydrogen, C1-4-alkyl, halogen, hydroxy, alkoxy, alkylsulfonyloxy or cyano.

Preferably, $R^a$ is hydrogen, methyl, hydroxy, methoxy, methylsulfonyloxy, a Br atom, a F atom or cyano. More preferably, $R^a$ is hydrogen, methyl, hydroxy or a F atom.

Generally, $R^b$ is hydrogen or C1-4-alkyl.

Preferably, $R^b$ is hydrogen or methyl. More preferably, $R^b$ is hydrogen.

In other preferred embodiments $R^a R^b$ is carbonyl.

Preferably, $NR^4R^5$ is a 5- to 9-membered heterocycle, which may be substituted, containing only one heteroatom which is a nitrogen atom or containing two heteroatoms wherein one is a nitrogen atom and the other is a non-oxidized sulfur atom. More preferably, $NR^4R^5$ is 1-azepanyl.

Combinations of one or more of these preferred compound groups are especially preferred.

More preferred compounds Ib are:

1-(6-azetidin-1-yl-2-cyclopropyl-5-methylpyrimidin-4-yl)azepane; 1-[2-cyclopropyl-5-methyl-6-(3-methylazetidin-1-yl)pyrimidin-4-yl]azepane; 1-(6-azepan-1-yl-2-cyclopropyl-5-methylpyrimidin-4-yl)azetidin-3-ol; 1-[2-cyclopropyl-6-(3-methylazetidin-1-yl)pyrimidin-4-yl]azepane; 1-(6-azetidin-1-yl-2-cyclopropylpyrimidin-4-yl)azepane and 1-[2-cyclopropyl-6-(3-fluoroazetidin-1-yl)-5-methylpyrimidin-4-yl]azepane, or pharmaceutically acceptable salts thereof.

Most preferred compounds Ib are:

1-(6-azetidin-1-yl-2-cyclopropyl-5-methylpyrimidin-4-yl)azepane and 1-[2-cyclopropyl-5-methyl-6-(3-methylazetidin-1-yl)pyrimidin-4-yl]azepane, or pharmaceutically acceptable salts thereof.

The present invention concerns also processes for preparing the compounds of formula I.

The following process description sets forth certain synthesis processes in an illustrative manner. Other alternative and/or analogous methods will be readily apparent to those skilled in this art.

A. According to one embodiment, compounds having the general formula I wherein $R^3$=H, alkyl, halogen, alkoxy or hydroxy may be prepared by reaction of a compound of formula II wherein $R^3$=H, alkyl, halogen, alkoxy or hydroxy with an amine of formula III according to the equation:

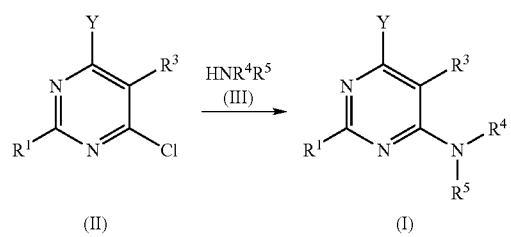

This reaction may be carried out without solvent in the case of high-boiling point amines of formula III or in a high-boiling point alcohol (e.g.: 1-methoxy-2-propanol) as solvent in the case of solid or low boiling point amines of formula III, between 80 and 130° C.

Compounds of formula III are commercially available or may be prepared under any conventional methods known to the person skilled in the art.

Compounds of formula II

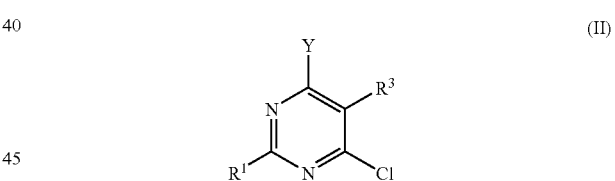

wherein $R^3$=H, alkyl, halogen, alkoxy or hydroxy may be prepared by reaction of a compound of formula IV wherein $R^3$=H, alkyl, halogen, alkoxy or hydroxy either with a primary amine of formula Va Reading to compounds IIa), or a with an azetidine of formula Vb (leading to compounds IIb) according to the equations:

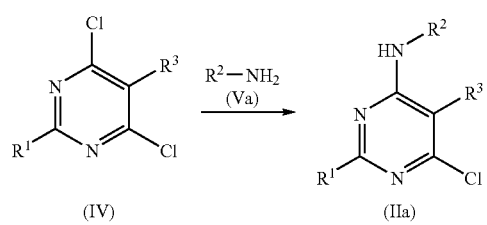

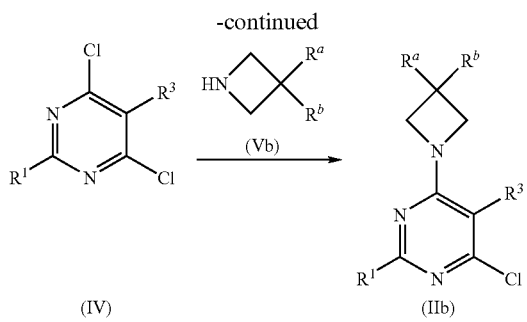

These reactions may be carried out without solvent or in dichloromethane as a solvent, between 30 and 60° C., in the presence of a base such as potassium carbonate in the case of an azetidine hydrochloride.

Compounds of formula Va are commercially available and compounds of formula Vb are either commercially available or may be prepared under any conventional method known to the person skilled in the art.

As an example, 3-fluoroazetidine hydrochloride may be prepared by catalytic hydrogenation of 1-benzhydryl-3-fluoroazetidine. This reaction can be performed by any person skilled in the art.

1-benzhydryl-3-fluoroazetidine may be prepared by fluoration of 1-benzhydryl-3-methanesulfonyloxy-azetidine. This reaction may be carried out in boiling acetonitrile in the presence of tetrabutylammonium fluoride as a fluorinating agent as described in: Berkin A., Szarek W. A., Kisilevsky R., Carbohydr. Res. (2000), 326, 250-263.

Compounds of formula IV wherein $R^3$=H, alkyl, halogen, alkoxy or hydroxy may be prepared by reaction of a compound of formula VI wherein $R^3$=H, alkyl, halogen, alkoxy or hydroxy with phosphorus oxychloride according to the equation:

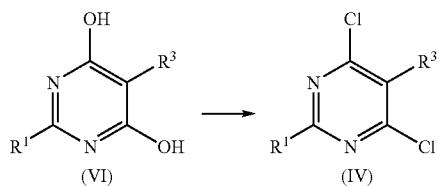

This reaction may be carried out in boiling phosphorus oxychloride in the presence of one equivalent of N,N-diethylaniline as described in: Evans R. F., Savage G. P., Gough D. A., Aust. J. Chem. (1990), 43, 733-740 or in: Biagi G., Giorgi I., Livi O., Scartoni V., Lucacchini A., Farmaco (1997), 52, 61-66.

Compounds of formula VI wherein $R^3$=H, ally, halogen, alkoxy or hydroxy may be prepared by reaction of a compound of formula VII with a dialkylmalonate of formula VIII wherein $R^3$=H, alkyl, halogen, alkoxy or hydroxy and $R^8$=C1-4-alkyl according to the equation:

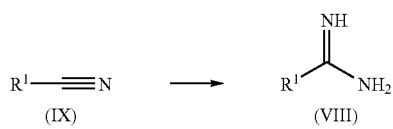

This reaction may be carried out in an alcoholic solvent, for example methanol or ethanol, in the presence of 2 equivalents of metallic sodium as a base between 60 and 80° C. as described in: Gershon H., Braun R., Scala A., Rodin R., J. Med. Chem. (1964), 7, 808.

Compounds of formula VIII are commercially available or may be prepared under any conventional method known to the person skilled in the art.

Compounds of formula VII are commercially available or may be prepared from the corresponding nitrile IX according to the equation:

$$R^1{-}{\equiv}N \longrightarrow R^1\underset{NH_2}{\overset{NH}{\diagup\!\!\!\diagdown}}$$

(IX)  →  (VIII)

This reaction may be carried out as described in: Moss R. A., Liu W., Krogh-Jespersen K., Tetrahedron Lett. (1993), 34, 6025-6028.

B. According to another embodiment, compounds having the general formula I wherein $R^3$=$NH_2$ may be prepared by reduction of the corresponding compound of formula I-A according to the equation:

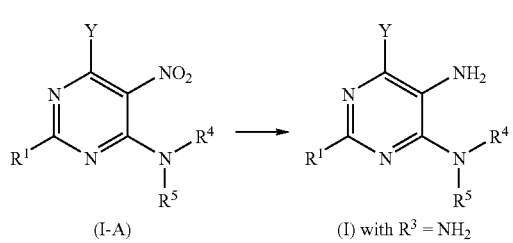

This reaction may be carried out by any conventional method known to the person skilled in the art, for example aqueous sodium dithionite in dioxane in the presence of ammonia as described in: Chorvat R. J. et al., J. Med. Chem. (1999), 42, 833-848.

Compounds of formula I-A wherein $R^3$=$NO_2$ may be prepared from a compound VI wherein $R^3$=$NO_2$ following the procedure described in A, using compound of formula

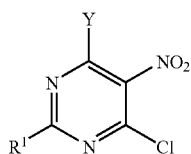

(II-A)

as an intermediate.

Compounds of formula VI wherein $R^3=NO_2$ may be prepared by reaction of the corresponding compound of formula VI wherein $R^3=H$ with nitric acid according to the equation:

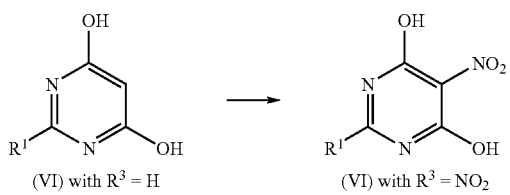

This reaction may be carried out using fuming nitric acid in glacial acetic acid between 30 and 40° C. as described in: Beck J. P. et al., Bioorg. Med. Chem. Lett. (1999), 9, 967 or in: Bagli J. et al., J. Med. Chem. (1988), 31, 814.

C. According to another embodiment, compounds having the general formula I wherein $R^3=Br$ may be prepared by bromination using N-bromosuccinimide (NBS) of a compound of formula I wherein $R^3=H$ according to the equation:

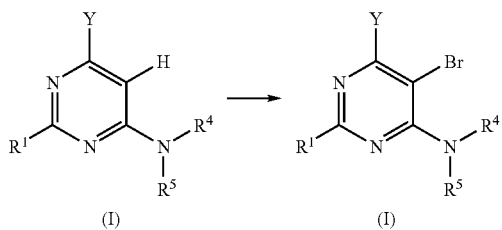

This reaction may be carried out in chloroform as described in: Chen C., Dagnino R., De Souza E. B., Grigoriadis, D. E., Huang C. Q., J. Med. Chem. (1996) 39, 4358-4360.

D. According to another embodiment, compounds having the general formula Ia wherein $R^2R^3$ is an alkylene bridging group of formula $—(CH_2)_n—CH_2—$, with n=1-6 may be prepared by reaction of a compound of formula X wherein n=1-6 with an amine of formula III according to the equation:

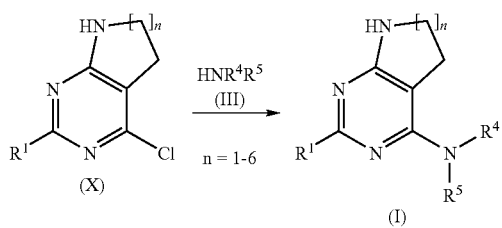

This reaction may be carried out without solvent in the case of high-boiling point amines of formula III or in a high-boiling point alcohol (e.g.: 1-methoxy-2-propanol) as solvent in the case of solid or low boiling point amines of formula III, between 80 and 130° C.

D.1 Compounds of formula X wherein n=2-6 may be prepared by heating a compound of formula IV wherein $R^3$ represents $—CH_2—(CH_2)_n—NH_2$ with n=2-6 according to the equation:

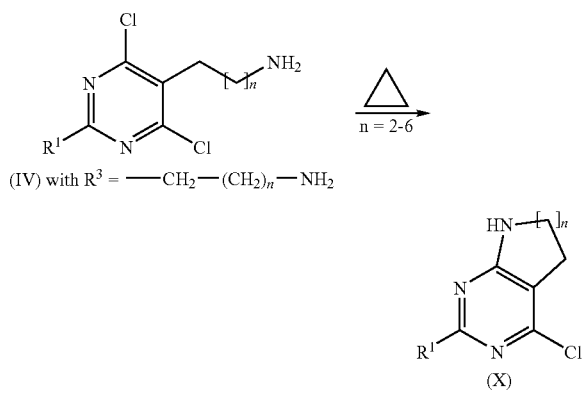

This reaction may be carried out in a high-boiling point alcohol (e.g.: 1-methoxy-2-propanol) as solvent, between 120 and 140° C.

Compounds of formula IV wherein $R^3$ represents $—CH_2—(CH_2)_n—NH_2$, with n=2-6, may be prepared by reaction of a compound of formula VI wherein $R^3$ represents $CH_2—(CH_2)_n—NHBoc$, with n=2-6, with phosphorus oxychloride according to the equation:

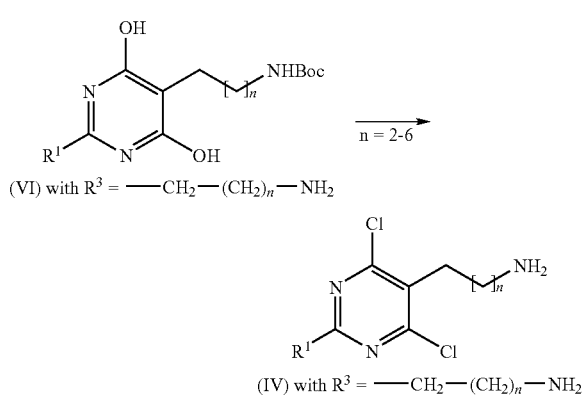

This reaction may be carried out in boiling phosphorus oxychloride in the presence of 1 equivalent of N,N-diethylaniline as described in Evans R. F., Savage G. P., Gough D. A., Aust. J. Chem. (1990), 43, 733-740 or in: Biagi G., Giorgi I., Livi O., Lucacchini A., Farmaco (1997), 52, 61-66.

Compounds of formula VI wherein $R^3$ represents $—CH_2—(CH_2)_n—NHBoc$, with n=2-6, may be prepared by reaction of a compound of formula VII with a dialkylmalonate of formula VIII wherein $R^3$ represents $—CH_2—(CH_2)_n—NHBoc$, with n=2-6, according to the procedure described in A.

Compounds of formula VIII wherein $R^3$ represents —$CH_2$—$(CH_2)_n$—NHBoc, with n=2-6, may be prepared by reaction the corresponding compound of formula VIII wherein $R^3$=H and $R^8$=C1-4-alkyl with a compound of formula XI wherein L is a leaving group according to the equation:

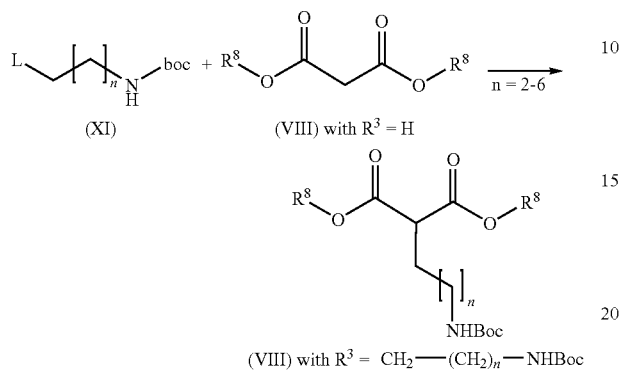

This reaction may be carried out starting from protected alkyl amines bearing a leaving group L (e.g.: halogen, mesylate) in an alcoholic solvent, for example methanol or ethanol, in the presence of 2 equivalents of metallic sodium as a base between 60 and 80° C.

Compounds of formula VIII are commercially available.

Compounds of formula XI may be prepared by any conventional methods known to the person skilled in the art.

D.2 Compounds of formula X wherein n=1 may be prepared by reaction of a compound of formula XII with phosphorus oxychloride according to the equation:

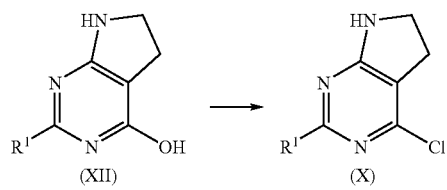

This reaction may be carried out in boiling phosphorus oxychloride.

Compounds of formula XII may be prepared by reaction of a compound of formula VII with 2-ethoxy-4,5-dihydro-3H-pyrrole-3-carboxylic acid ethyl ester (XII) according to the equation:

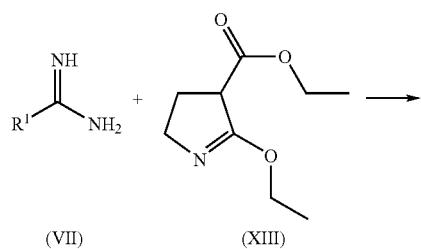

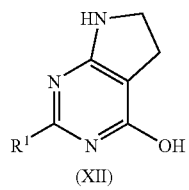

This reaction may be carried out in an alcoholic solvent, for example methanol or ethanol, in the presence of 1 equivalent of metallic sodium as a base between 60 and 80° C. as described in: Gershon H., Braun R., Scala A., Rodin R., J. Med. Chem. (1964), 7, 808 and in: Granik V. G., Glushkov R. G., Pharm. Chem. J. (Engl. Transl.) (1967), 5, 247-249.

2-Ethoxy-4,5-dihydro-3H-pyrrole-3-carboxylic acid ethyl ester of formula (XIII) may be prepared as described in: Granik V. G., Glushkov R. G., Pharm. Chem. J. (Engl. Transl.) (1967), 5, 247-249 and in: Lindstrom K. J., Crooks S. L., Synth. Commun. (1990), 2335-2337.

E. According to another embodiment, compounds having the general formula Ib wherein $R^a$=Br may be prepared by bromination using sodium bromide of a compound of formula Ib wherein $R^a$=$OSO_2CH_3$ according to the equation:

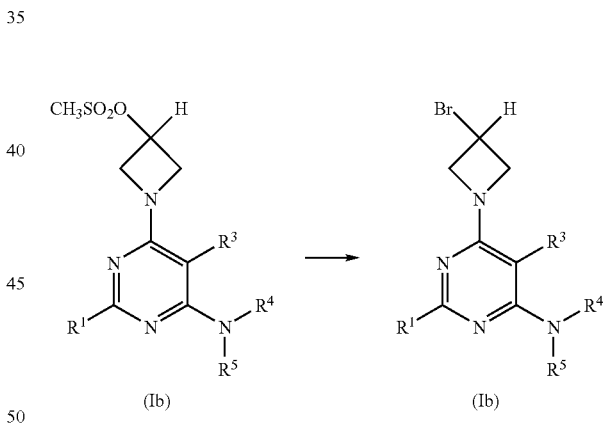

This reaction may be carried out in N,N-dimethylformamide between 80 and 120° C. as described in: Okada T., Ezumi K., Yamakawa M., Sato H., Tsuji T., Chem Pharm. Bull. (1993), 41, 126-131.

Compounds having the general formula Ib wherein $R^a$=$OSO_2CH_3$ may be prepared by mesylation using methanesulfonyl chloride of a compound of formula Ib wherein $R^a$=OH. This reaction may be carried out by any person skilled in the art.

F. According to another embodiment, compounds having the general formula Ib wherein $R^a$=CN may be prepared by cyanation using sodium cyanide of a compound of formula Ib wherein $R^a$=$OSO_2CH_3$ according to the equation:

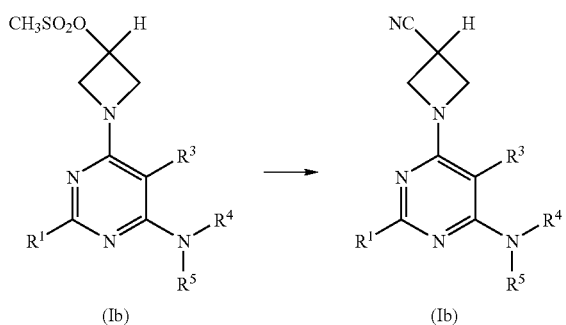

This reaction may be carried out in N,N-dimethylformamide between 80 and 120° C. as described in: Frigola J., Pares J., Corbera J., Vano D., Merce R., J. Med. Chem. (1993), 36, 801-810.

G. According to another embodiment, compounds having the general formula Ib wherein $R^aR^b$=carbonyl may be prepared by oxidation using sulfur trioxide/pyridine complex of a compound of formula Ib wherein $R^a$=OH according to the equation:

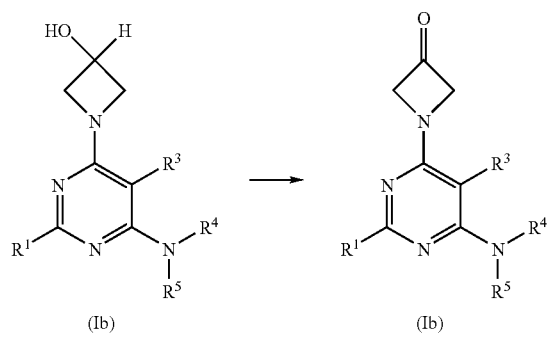

This reaction may be carried out in dimethylsulfoxide at room temperature as described in: Katritzky A. R., Cundy D. J., Chen J., J. Heterocyclic Chem. (1994), 31, 271-276.

When compounds of formula I present one or several stereogenic centres, and that non-stereoselective methods of synthesis are used, resolution of the mixture of stereoisomers can best be effected in one or several steps, involving generally sequential separation of mixtures of diastereomers into their constituting racemates, using preferably chromatographic separations on achiral or chiral phase in reversed or preferably in direct mode, followed by at least one ultimate step of resolution of each racemate into its enantiomers, using most preferably chromatographic separation on chiral phase in reversed or preferably in direct mode. Alternatively, when partly stereoselective methods of synthesis are used, the ultimate step may be a separation of diastereomers using preferably chromatographic separations on achiral or chiral phase in reversed or preferably in direct mode.

In another embodiment, the present invention concerns also the synthesis intermediates of formula II

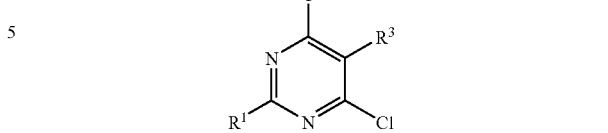

wherein Y, $R^1$ and $R^2$ are as defined above, $R^3$ is hydrogen, alkyl, halogen, alkoxy or hydroxy, $R^a$ is hydrogen, alkyl, alkenyl, alkynyl, halogen, hydroxy, alkoxy, amino, alkylamino, alkylsulfonyloxy, cyano, carboxy, ester or amido, and $R^b$ is hydrogen, alkyl or halogen or $R^aR^b$ is carbonyl.

In synthesis intermediates of formula II, when Y represents a group of formula

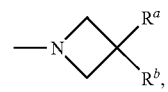

then $R^1$ is preferably cycloalkyl, more preferably cyclopropyl and $R^3$ is preferably hydrogen or alkyl, more preferably hydrogen or methyl.

In a preferred embodiment, the present invention also concerns the synthesis intermediates selected from the group consisting of 6-chloro-N,2-dicyclopropyl-5-fluoro-4-pyrimidinamine; 6-chloro-N,2-dicyclopropyl-4-pyrimidinamine; 6-chloro-N,2-dicyclopropyl-5-methyl-4-pyrimidinamine; 5,6-dichloro-N,2-dicyclopropyl-4-pyrimidinamine; 6-chloro-N,2-dicyclopropyl-5-methoxy-4-pyrimidinamine; 6-chloro-N,2-dicyclopropyl-5-ethyl-4-pyrimidinamine; N-[6-chloro-2-(2-trans-methylcyclopropyl)-4-pyrimidinyl]-N-cyclopropylamine and its enantiomers; 6-chloro-N-cyclopropyl-5-methyl-2-(2-trans-methylcyclopropyl)-4-pyrimidinamine; 6-chloro-N-cyclopropyl-5-methyl-2-(2-cis-methylcyclopropyl)-4-pyrimidinamine; N-[6-chloro-2-(cyclopropylmethyl)-5-methyl-4-pyrimidinyl]-N-cyclopropylamine; 6-chloro-2-cyclobutyl-N-cyclopropyl-5-methyl-4-pyrimidinamine; 6-chloro-N-cyclobutyl-2-cyclopropyl-5-methyl-4-pyrimidinamine; 6-chloro-N-cyclopropyl-2-isopropyl-5-methyl-4-pyrimidinamine; 6-chloro-2-cyclopentyl-N-cyclopropyl-5-methyl-4-pyrimidinamine; 6-chloro-2-cyclopropyl-5-methyl-N-(2-methylcyclopropyl)-4-pyrimidinamine; 6-chloro-2-cyclopropyl-5-methyl-N-(1-methylcyclopropyl)-4-pyrimidinamine; 6-chloro-2-cyclopropyl-5-methyl-N-(2-phenylcyclopropyl)-4-pyrimidinamine; 4-(1-azetidinyl)-6-chloro-2-cyclopropyl-5-methylpyrimidine; 4-(1-azetidinyl)-6-chloro-2-cyclopropylpyrimidine; 4-chloro-2-cyclopropyl-5-methyl-6-(3-methyl-1-azetidinyl)pyrimidine; 4-chloro-2-cyclopropyl-6-(3-methyl-1-azetidinyl)pyrimidine; 4-chloro-2-cyclopropyl-6-(3,3-dimethyl-1-azetidinyl)-5-methylpyrimidine; 1-(6-chloro-2-cyclopropyl-5-methyl-4-pyrimidinyl)-3-azetidinol; 4-chloro-2-cyclopropyl-6-(3-fluoro-1-azetidinyl)-5-methylpyrimidine; 4-chloro-2-cyclopropyl-6-(3-fluoro-1-azetidinyl)pyrimidine and 4-chloro-2-cyclopropyl-6-(3-methoxy-1-azetidinyl)-5-methylpyrimidine.

In another embodiment, the present invention concerns the following synthesis intermediate of formula II-A: 6-chioro-N,2-dicyclopropyl-5-nitro-4-pyrimidinamine.

In another embodiment, the present invention concerns the following synthesis intermediate of formula VII: 2-methylcyclopropanecarboximidamide.

In another embodiment, the present invention concerns the synthesis intermediates of formula VI

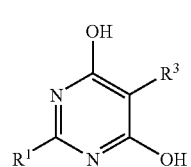

(VI)

wherein $R^1$ is alkyl or cycloalkyl and $R^3$ is alkoxy. Usually, $R^1$ is alkyl or C3-5-cycloalkyl.

In a preferred embodiment, the present invention also concerns the synthesis intermediates selected from the group consisting of: 2-cyclopropyl-5-fluoro-4,6-pyrimidinediol; 5-chloro-2-cyclopropyl-4,6-pyrimidinediol; 2-cyclopropyl-5-methoxy-4,6-pyrimidinediol; 2-cyclopropyl-5-ethyl-4,6-pyrimidinediol; 2-(2-methylcyclopropyl)-4,6-pyrimidinediol; 5-methyl-2-(2-methylcyclopropyl)-4,6-pyrimidinediol; 2-(cyclopropylmethyl)-5-methyl-4,6-pyrimidinediol; 2-cyclobutyl-5-methyl-4,6-pyrimidinediol; 2-isopropyl-5-methyl-4,6-pyrimidinediol; 2-cyclopentyl-5-methyl-4,6-pyrimidinediol; [3-(2-cyclopropyl-4,6-dihydroxy-pyrimidin-5-yl)-propyl]-carbamic acid tert-butyl ester and [4-(2-cyclopropyl-4,6-dihydroxy-pyrimidin-5-yl)-butyl]-carbamic acid tert-butyl ester.

In another embodiment, the present invention concerns the following synthesis intermediates of formula IV: 4,6-dichloro-2-cyclopropyl-5-fluoropyrimidine; 4,5,6-trichloro-2-cyclopropylpyrimidine; 4,6-dichloro-2-cyclopropyl-5-pyrimidinyl methyl ether; 4,6-dichloro-2-cyclopropyl-5-ethylpyrimidine; 4,6-dichloro-2-(2-methylcyclopropyl) pyrimidine; 4,6-dichloro-5-methyl-2-(2-methylcyclopropyl) pyrimidine; 4,6-dichloro-2-(cyclopropylmethyl)-5-methylpyrimidine; 4,6-dichloro-2-cyclobutyl-5-methylpyrimidine; 4,6-dichloro-2-isopropyl-5-methylpyrimidine and 4,6-dichloro-2-cyclopentyl-5-methylpyrimidine.

In another embodiment, the present invention concerns the following synthesis intermediate of formula I-A: 6-(1-azepanyl)-N,2-dicyclopropyl-5-nitro-4-pyrimidinamine.

In another embodiment, the present invention concerns the synthesis intermediates of formula X

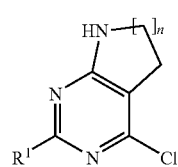

(X)

wherein n is 1-6 and $R^1$ is cycloalkyl.

Preferably, the synthesis intermediates of formula X are selected from the group consisting of: 4-chloro-2-cyclopropyl-6,7-dihydro-5H-pyrrolo[2,3-d]pyrimidine; 4-chloro-2-cyclopropyl-5,6,7,8-tetrahydro-5H-pyrido[2,3-d]pyrimidine and 4-chloro-2-cyclopropyl-6,7,8,9-tetrahydro-5H-pyrimido[4,5-b]azepine.

In another embodiment, the present invention concerns the synthesis intermediates of formula XII

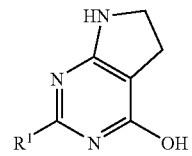

(XII)

wherein $R^1$ is cycloalkyl.

Preferably, the synthesis intermediate of formula XII is 2-cyclopropyl-6,7-dihydro-5H-pyrrolo[2,3-d]pyrimidin-4-ol.

It has now been found that compounds of formula I and their pharmaceutically acceptable salts are useful in a variety of pharmaceutical indications.

For example, the compounds according to the invention are useful for the treatment of respiratory disorders in connection with the Chronic Obstructive Pulmonary Disease (COPD).

These compounds may also be used for treating symptoms related to disorders such as chronic bronchitis, emphysema, cough, either directly linked to COPD or not, and also cystic fibrosis, pulmonary fibrosis, adult respiratory distress syndrome, rhinitis and asthma.

Preferred compounds have antagonist activity against the human m3 muscarinic receptor at concentrations ranging from 100 nM to almost 1 nM and incorporate activity as selective phosphodiesterase IV (PDE IV) inhibitors at concentrations ranging from 2.5 µM to almost 50 nM. These compounds also recognize the m1, m2, m4 and m5 receptors with variable receptor subtype selectivity.

Preferred compounds have been proven to antagonise carbachol-induced contraction of guinea-pig trachea in vitro.

In addition the compounds according to the invention may be used in the treatment of the following symptoms which are related to PDE IV or $M_3$:

PDE IV-Related

Amongst PDEs, PDE IV is highly selective for cAMP. Four human PDE IV subtypes have been identified, with distinct tissue and cellular distribution. PDE IVA appears to be distributed ubiquitously. PDE IVB is expressed in heart, brain, skeletal muscle and lung. PDE IVC is abundant in neuronal tissue but is absent from immune and inflammatory cells. PDE IVD is abundant in immune and inflammatory cells. Functional effects such as those associated with gastric acid secretion, relaxation of the myometrium, bronchorelaxation and diuresis in the kidney have been attributed to the effect of PDE IV inhibition. This argues in favour of the interest of such approach for treating GI disorders, kidney dysfunction, respiratory and inflammatory disorders.

Furthermore, PDE IV may also be of biological significance and therapeutic relevance in CNS therapeutic indications such as depression and dementia. The hypothesis is that enhanced cAMP availability produced by inhibition of PDE IV stimulates the increase in noradrenaline function produced by classical antidepressants such as imipramine at the post-synaptic level (Wachtel H., Pharmacopsychiatry (1990), 23, 27-32). Denbufylline has also been shown to increase cAMP in cortical slices, indicating a potential in the treatment of cognitive impairment (Nicholson C. D., Psychopharmacology (1990), 101, 147-159).

In addition, the PDE IV enzyme may also be a potential target for anticancer therapy, due to its inhibitory effect on tumour cell growth (Drees M., Zimmermann R, Eisenbrand G., Cancer Res. (1993), 53, 3058-3061), and PDE IV inhibition may be beneficial in tissue transplantation (Pinsky D., Oz M., Morris S., J. Clin. Invest. (1993), 92, 2994-3002) and for cardiovascular diseases including atherosclerosis and hypertension (Demoullou-Mason C., Exp. Opin. Ther. Patents (1994), 4, 813-823).

$M_3$-Related

Lower Urinary Tract Disorders:

The parasympathetic nervous system is the principal excitatory innervation to the detrusor smooth muscle of the urinary bladder. Acetylcholine, released from postganglionic cholinergic nerves, activates post-junctional muscarinic receptors in the detrusor which causes contraction of the bladder that is coordinated with outlet relaxation and leads to voiding of urine (De Groat W. C., Booth A. M., Yoshimura N., In: "Nervous control of the urogenital system", Maggi, C. A. (Ed), Harwood Academic Publishers, Amsterdam, (1993), 227-290). Both m2 and m3 muscarinic receptors are expressed in the smooth muscle of the bladder detrusor (Hegde S. S., Eglen R. M., Life Science (1999), 64, 419-428). Muscarinic m3 receptors play a key role in mediating the contractile effect of Acetylcholine (ACh) but m2 receptors may also contribute to micturition through opposing the relaxing effect of adrenergic sympathetic tone. Prejunctional m1 facilitory muscarinic receptors may also be involved.

Aging, inflammation or irritants and neurological trauma may result in increased nerve afferent and efferent activity and overactive bladder to become a leading cause of trouble presenting some symptoms such as urgency and frequency micturation and incontinence.

Therefore, non-selective muscarinic $M_3$ antagonists have utility in the treatment of bladder disorders including urge and mixed urinary incontinence, pollakiuria, neurogenic or unstable bladder, hyperreflexia and chronic cystitis (Gillberg P. G., Sundquist S., Nilvebrant L., Eur. J. Pharmacol. (1998), 349, 285-292; Schwantes U., Topfmeler P., International Journal of Clinical Pharmacology and Therapeutics (1999), 37, 209-218; Andersson K. E. et al., In: "Incontinence. 1st International Consultation on Incontinence—Jun. 28-Jul. 1, 1998—Monaco", Abrams P., Khouri S., Wein A., Les Editions Vingt et Un, Paris, (1999), 447-486).

Gastrointestinal Disorders:

Contractility of the smooth muscle of the gastrointestinal tract is under the control of parasympathetic tone and Acetylcholine (ACh). Contraction of the intestinal smooth muscle is principally dependent upon activation of muscarinic m3 receptors although stimulation of m2 muscarinic receptors might synergize with m3-mediated responses (Sawyer G. W., Ehlert F. J., J. Pharmacol. Exp. Ther. (1998), 284, 269-277).

Gastric secretion is also under the control of the parasympathetic nervous system. Secretagogue effect of ACh depend on the activation of post-junctional m3 receptors whilst m1 receptors located on the post-ganglionic nerves of the myenteric plexus have a facilatory role on the parasympathetic nerve activity.

Therefore, $m_3$ and $m_1$ muscarinic receptor antagonists are potentially useful for treating gastrointestinal disorders associated with intestinal hypermotility such as irritable bowel syndrome, spastic colitis and diverticulosis (Wailis R. M., Napier C. M., Life Science (1999), 64, 395-401) and to reduce acid secretion, gastric motility, to aid the healing of peptic ulcers and to treat gastroesophageal reflux disease and stress-related erosive syndrome (Rademaker J. W., Hunt R. H., Scand. J. Gastroenterol. (1990), 25, 19-26; Coruzzi G., Adami M., Bertaccini G., Arch. Int. Pharmacodyn. Ther. (1989), 302, 232-241).

CNS—Cognitive Disorders

The release of acetylcholine from central cholinergic nerves is under autoinhibitory control via m2 or m4 autoreceptors.

Therefore, $M_2$ or $M_4$ antagonists might reduce the levels of ACh released and may offer a potential approach for the treatment of cognitive disorders causally related to a deterioration or deficit of cortical cholinergic neurons, such as in senile dementia and Alzheimer's disease (Doods H. N., Quinrion R., Mihm G., Life Science (1993), 52, 497-503).

CNS—Locomotor Disorders

The nigrostriatum has many more m4 receptors than any other tissue (Santiago M. P., Potter L. T., Brain Res. (2001), 894, 12-20). These receptors exert inhibitory control on Dopamine (D1) receptor mediated locomotor stimulation (Gomeza J., Zhang L., Kostenis E., Felder C., Bymaster F., Brodkin J., Shannon H., Xia B., Deng C., Wess J., Proc. Natl. Acad. Sci. USA. (1999), 96, 10483-10488).

Therefore, centrally active $M_4$ muscarinic antagonists may have the potential to treat Parkinsonian's disorders and dyskinesia thought to be causally related to a deterioration of dopaminergic neurons in the nigrostriatum (Salamone J. D., Carlson B. B., Correa M., Wisniecki A., Nisenbaum E., Nisenbaum L., Felder C., In: "Society for Neuroscience $30^{th}$ Annual Meeting New Orleans, November 2000", Mayorga et al., (1999), Abstract 278.5; Mayorga A. J., Cousins M. S., Trevitt J. T., Conlan A., Gianutsos G., Salamone J. D., Eur. J. Pharmacol. (1999), 364, 7-11).

CNS—Feeding Disorders

Activation of muscarinic m3 receptors located in the lateral hypothalamus contributes to feeding behaviour (Yamada M. et al., Nature (2001), 410, 207-212).

Thereby, $M_3$ antagonists may offer new therapeutic perspectives for the treatment of obesity, bulimia and metabolic syndrome.

CNS—Sleeping Disorders

Activation of m1 and m3 receptors in the mediodorsal pontine tegmentum results in a marked increased in paradoxical sleep indicating that centrally active $M_3$ antagonists can be useful for treating sleep disorders (Imeri L., Bianchi S., Angeli P., Mancia M., Brain Res. (1994), 636, 68-72; Sakai, K., Onoe H., Eur. J. Neurosci. (1997), 9, 415-23).

Cardiovascular Disorders

The heart rate is under parasympathetic tone via muscarinic m2 receptors on the SA node.

Therefore, $m_2$ receptor antagonists are of potential value in the emergency treatment of acute myocardial infarction where the dominant autonomic influence of the heart is via the vagus nerve, causing sinus or nodal bradycardia (Van Zwieten P. A., Doods H. N., Cardiovascular Drugs and Therapy (1995), 9, 159-167).

Thus the present invention concerns a compound of formula I or a pharmaceutically acceptable salt thereof for use as a medicament.

In a further aspect, the present invention concerns the use of a compound of formula I or a pharmaceutically acceptable salt thereof for the manufacture of a medicament for the treatment of PDE IV and/or $M_3$ related disorders such as mentioned above.

In particular, the present invention concerns the use of a compound of formula I or a pharmaceutically acceptable salt thereof for the manufacture of a medicament for the treatment of COPD or of symptoms related to disorders such as chronic bronchitis, emphysema, cough, cystic fibrosis, pulmonary fibrosis, adult respiratory distress syndrome, rhinitis and asthma.

The present invention also concerns a method for treating COPD or symptoms related to disorders such as chronic bronchitis, emphysema, cough, cystic fibrosis, pulmonary fibrosis, adult respiratory distress syndrome, rhinitis and asthma in a mammal in need of such treatment, comprising administering at least one compound of formula I or a pharmaceutically acceptable salt thereof to a patient.

The term "treatment" as used herein includes curative treatment and prophylactic treatment. By "curative" treatment is meant efficacy in treating a current symptomatic episode of a disorder or condition. By "prophylactic" treatment is meant prevention of the occurrence or recurrence of a disorder or condition.

For treating diseases, compounds of formula I, or their pharmaceutically acceptable salts, may be employed at an effective daily dosage and administered in the form of a pharmaceutical composition.

Therefore, another embodiment of the present invention concerns a pharmaceutical composition comprising an effective amount of a compound of formula I or a pharmaceutically acceptable salt thereof in combination with a pharmaceutically acceptable diluent or carrier.

To prepare a pharmaceutical composition according to the invention, one or more of the compounds of formula I or a pharmaceutically acceptable salt thereof, is intimately admixed with a pharmaceutical diluent or carrier according to conventional pharmaceutical techniques known to the skilled practitioner.

Pharmaceutical compositions comprising compounds according to the invention can, for example, be administered orally or parenterally, i.e., intravenously, intramuscularly, subcutaneously or by inhalation (orally or intranasally). In a preferred embodiment, the pharmaceutical compositions are administered by inhalation.

Pharmaceutical compositions suitable for oral administration can be solids or liquids and can, for example, be in the form of tablets, pills, dragees, gelatin capsules, solutions, syrups, aerosols, powders for inhalation and the like. Pharmaceutical compositions suitable for administration by inhalation are preferred.

The following examples are provided for illustrative purposes.

Unless otherwise specified in the examples, characterization of the compounds was performed according to the following methods:

NMR spectra are recorded on a BRUKER AC 250 Fourier Transform NMR Spectrometer fitted with an Aspect 3000 computer and a 5 mm $^1H/^{13}C$ dual probehead or BRUKER DRX 400 FT NMR fitted with a SG Indigo2 computer and a 5 mm inverse geometry $^1H/^{13}C/^{15}N$ triple probehead. The compound is studied in DMSO-$d_6$ (or CDCl$_3$) solution at a probe temperature of 313 K and at concentrations ranging from 2 to 20 mg/ml. The instrument is locked on the deuterium signal of DMSO-$d_6$ (or CDCl$_3$). Chemical shifts are given in ppm downfield from TMS taken as internal standard.

Mass Spectrometric Measurements in LC/MS Mode are Performed as Follows:

HPLC Conditions

Analyses are performed using a WATERS Alliance HPLC system mounted with an INERTSIL ODS 3-, DP 5 µm, 250× 4.6 mm column.

The gradient runs from 100% solvent A (acetonitrile, water, TFA (10/90/0.1, v/v/v)) to 100% solvent B (acetonitrile, water, TFA (90/10/0.1, v/v/v)) in 7 min with a hold at 100% B of 4 min. The flow rate is set at 2.5 ml/min and a split of 1/10 is used just before API source. The chromatography is carried out at 30° C.

MS Conditions

Samples are dissolved in acetonitrile/water, 70/30, v/v at the concentration of about 250 µg/ml. API spectra (+ or −) are performed using a FINNIGAN (San Jose, Calif., USA) LCQ ion trap mass spectrometer. APCI source operates at 450° C. and the capillary heater at 160 C. ESI source operates at 3.5 kV and the capillary heater at 210° C.

Mass spectrometric measurements in EI/DIP mode are performed as follows: samples are vaporized by heating the probe from 50° C. to 250° C. in 5 min. EI (Electron Impact) spectra are recorded using a FINNIGAN (San Jose, Calif., USA) TSQ 700 tandem quadrupole mass spectrometer. The source temperature is set at 150° C.

Specific rotation is recorded on a Perkin-Elmer MC241 or MC341 polarimeter. The angle of rotation is recorded at 25° C. on 1% solutions in MeOH. For some molecules, the solvent is $CH_2Cl_2$ or DMSO, due to solubility problems.

Water content is determined using a Metrohm microcoulometric Karl Fischer titrator.

Preparative chromatographic separations are performed on silicagel 60 Merck, particle size 15-40 µm, reference 1.15111.9025, using in-house modified Jobin Yvon-type axial compression columns (80 mm i.d.), flow rates between 70 and 150 ml/min. Amount of silicagel and solvent mixtures are as described in individual procedures.

Preparative chiral chromatographic separations are performed on a DAICEL Chiralpak AD 20 µm, 100*500 mm column using an in-house build instrument with various mixtures of lower alcohols and C5 to C8 linear, branched or cyclic alkanes at ±350 ml/min. Solvent mixtures are as described in individual procedures.

Melting points are determined on a Büchi 535 or 545 Tottoli-type fusionometre, and are not corrected, or by the onset temperature on a Perkin Elmer DSC 7.

Unless specified otherwise in the examples, the compounds are obtained in the neutral form.

In the tables, the stereochemical information is contained in the three columns headed 'configuration data'. The second column indicates whether a compound has no stereogenic center (ACHIRAL), is a pure configuration isomer or enantiomer (PURE), a racemate (RAC) or is a mixture of two or more stereoisomers, possibly in unequal proportions (MIXT). The first column contains the stereochemical assignment for each recognised center, following the IUPAC numbering used in the preceding column. A number alone indicates the existence of both configurations at that center. A number followed by 'R' or 'S' indicates the known absolute configuration at that center. A number followed by '§' indicates the existence of only one but unknown absolute con figuration at that center. The letter (A, B, C, D) in front is a way of distinguishing the various configuration isomers, enantiomers or racemates of the same structure. The third column precises the cis or trans isomerism.

In the tables, the melting points are in most cases determined by the onset of the DSC curve. When a visual (fusionometer) melting point is given, the value is between brackets.

EXAMPLE 1

Synthesis of Amidines of Formula VII 1.1 Synthesis of 2-methylcyclopropanecarbonitrile 1

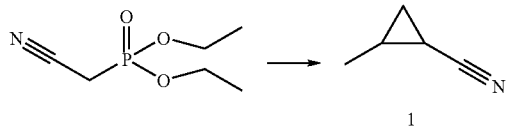

To a suspension of sodium hydride (11 g, 0.28 mol, 60% in oil, washed two times with n-hexane) in tetrahydrofuran (150 ml) is added diethyl cyanomethylphosphonate (45.5 g, 0.25 mol) over 0.5 h, at room temperature. The mixture is stirred 0.25 h. Propylene oxide (16.3 g, 0.28 mol) is added dropwise at room temperature and the solution is stirred for 1 h then heated at reflux for 4 h. The mixture is cooled and ammonium chloride (115 g) is added. The solvent is distilled, the residue is poured onto crushed ice and extracted three times with diethyl ether. The combined organic layers are washed with brine, dried over magnesium sulfate, concentrated (atmospheric pressure) and the final residue is distilled under reduced pressure (75° C., 70 mm Hg) to afford pure 2-methylcyclopropanecarbonitrile 1 (7.5 g, 33%) as an oil.

1.2 Synthesis of 2-methylcyclopropanecarboximidamide Hydrochloride 2

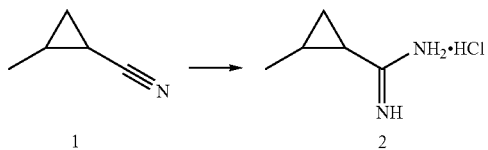

Gaseous hydrochloric acid is passed through a solution of 2-methylcyclopropanecarbonitrile 1 (7.5 g, 92 mmol) in ethanol (8.5 ml) at 0° C. until 7 g have been absorbed. The resulting mixture is kept in the refrigerator for 48 h. Ethanol (150 ml) is then added and gaseous ammonia is passed through the solution at −5° C. for 4 h. The solvent is evaporated in vacuo. Hydrochloric acid in diethyl ether (3 N solution, 3 ml) is added and the solution is concentrated and dried in vacuo to afford 2-methylcyclopropanecarboximidamide hydrochloride 2 (6.15 g, 50%) as a paste that is used without further purification.

EXAMPLE 2

Synthesis of 4,6-pyrimidinediol Derivatives of Formula VI 2.1 Synthesis of 2-cyclopropyl-5-fluoro-4,6-pyrimidinediol 3

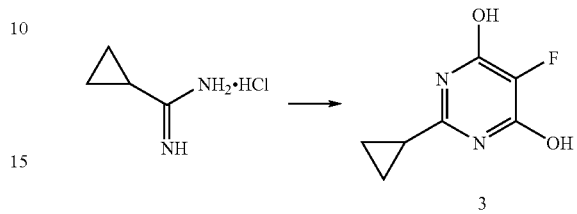

Sodium (646 mg, 28 mmol) is dissolved in methanol (50 ml) under a nitrogen atmosphere. Cyclopropanecarboximidamide hydrochloride (3.40 g, 28 mmol) is added in one portion. The mixture is stirred at room temperature for 0.25 h, then filtered upon hyflocel. The filtrate is concentrated in vacuo. This free base is added to a solution of sodium (1.29 g, 56 mmol) in methanol (50 ml) under a nitrogen atmosphere, at room temperature. Diethylfluoromalonate (5 g, 28 mmol) is added and the mixture is stirred at 60° C. for 5 h. The solvent is evaporated and the yellowish solid obtained is dissolved in 60 ml of water. The pH is adjusted at 6 with a 5 N HCl solution and the white precipitate formed is filtered and dried. 2-cyclopropyl-5-fluoro-4,6-pyrimidinediol 3 (3.6 g, 76%) is obtained as a white powder and used in the next step without further purification.

$^1$H NMR (250 MHz, DMSO): 0.95 (m, 4H), 1.83 (m, 1H), 12.1 (bs, 2H).

Compounds described in table 1 can be synthesized in an analogous way.

TABLE 1

| | | |
|---|---|---|
| 4 | 2-cyclopropyl-4,6-pyrimidinediol | Patent Geigy 1966, NL6513321 |
| 5 | 2-cyclopropyl-5-methyl-4,6-pyrimidinediol | MS(M$^+$·): 166 |
| 6 | 5-chloro-2-cyclopropyl-4,6-pyrimidinediol | MS(M$^+$·): 187/189 |
| 7 | 2-cyclopropyl-5-methoxy-4,6-pyrimidinediol | MS(M$^+$·): 182 |
| 8 | 2-cyclopropyl-5-ethyl-4,6-pyrimidinediol | MS(M$^+$·): 180 |
| 9 | 2-(2-methylcyclopropyl)-4,6-pyrimidinediol | $^1$H NMR(250 MHz, DMSO): 0.83(m, 1H), 1.11(d, 3H), 1.18(m, 1H), 1.38(m, 1H), 1.61(m, 1H), 5.03(s, 1H) |
| 10 | 5-methyl-2-(2-methylcyclopropyl)-4,6-pyrimidinediol | MS(MH$^+$): 181 |
| 11 | 2-(cyclopropylmethyl)-5-methyl-4,6-pyrimidinediol | MS(MH$^+$): 181 |
| 12 | 2-cyclobutyl-5-methyl-4,6-pyrimidinediol | MS(M$^+$·): 180 |
| 13 | 2-isopropyl-5-methyl-4,6-pyrimidinediol | MS(MH$^+$): 169 |
| 14 | 2-cyclopentyl-5-methyl-4,6-pyrimidinediol | MS(M$^+$·): 194 |
| 15 | [3-(2-cyclopropyl-4,6-dihydroxy-pyrimidin-5-yl)-propyl]-carbamic acid tert-butyl ester | MS(MH$^+$): 310 |
| 16 | [4-(2-cyclopropyl-4,6-dihydroxy-pyrimidin-5-yl)-butyl]-carbamic acid tert-butyl ester | MS(MH$^+$): 324 |

2.2 Synthesis of 2-cyclopropyl-5-nitro-4,6-pyrimidinediol 17

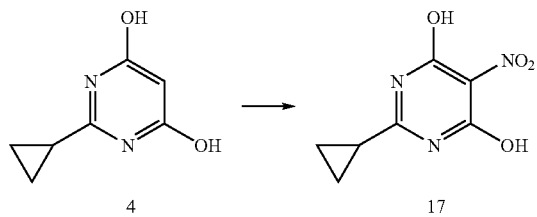

Glacial acetic acid (90 ml) is added to fuming nitric acid (40 ml) at 0° C. The solution is warmed to 30° C. and 2-cyclopropyl-4,6-pyrimidinediol 4 (35 g, 0.25 mol) is added in portions. The temperature is kept between 30 and 40° C. After 1 h, the mixture is poured onto crushed ice and filtered. The filtrate is concentrated to 50 ml in vacuo. Methanol is added and the precipitate is filtered and dried. Pure 2-cyclopropyl-5-nitro-4,6-pyrimidinediol 17 (39.8 g, 81%) is obtained and used in the next step without further purification.

MS (M$^+$.): 197.

EXAMPLE 3

Synthesis of 4,6-dichloropyrimidine Derivatives of Formula IV

3.1 Synthesis of 4,6-dichloro-2-cyclopropyl-5-fluoropyrimidine 18

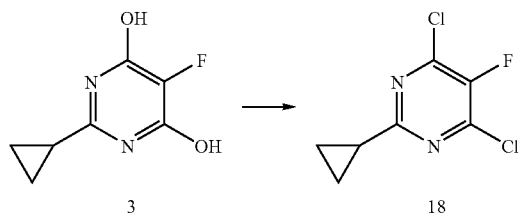

2-cyclopropyl-5-fluoro-4,6-pyrimidinediol 3 (3.51 g, 21 mmol) is suspended in phosphorus oxychloride (15 ml). A mixture of N,N-diethylaniline (3.08 g, 21 mmol) and phosphorus oxychloride (15 ml) is added dropwise to the suspension at 0° C. The resulting mixture is stirred at 110° C. for 2 h, then cooled to room temperature. The brown solution is poured onto crushed ice and extracted five times with dichloromethane. The combined organic layers are washed three times with a 1 N HCl solution, dried over magnesium sulfate and concentrated in vacuo to afford 4,6-dichloro-2-cyclopropyl-5-fluoropyrimidine 18 as an orange oil (4.80 g, 100%) which is used in the next step without further purification.

MS (M$^+$.): 205/207/209.

Compounds described in table 2 can be synthesized in an analogous way.

TABLE 2

| | | |
|---|---|---|
| 19 | 4,6-dichloro-2-cyclopropylpyrimidine | MS(M$^+$.): 189/191/193 |
| 20 | 4,6-dichloro-2-cyclopropyl-5-methylpyrimidine | MS(M$^+$.): 202/204/206 |
| 21 | 4,5,6-trichloro-2-cyclopropylpyrimidine | MS(M$^+$.): 222/224/226 |
| 22 | 4,6-dichloro-2-cyclopropyl-5-pyrimidinyl methyl ether | MS(M$^+$.): 218/220/222 |
| 23 | 4,6-dichloro-2-cyclopropyl-5-ethylpyrimidine | $^1$H NMR(250 MHz, CDCl$_3$): 1.12(m, 4H), 1.20(t, 3H), 2.16(m, 1H), 2.85(q, 2H) |
| 24 | 4,6-dichloro-2-(2-methylcyclopropyl)pyrimidine | eb. = 85° C./1 mmHg |
| 25 | 4,6-dichloro-5-methyl-2-(2-methylcyclopropyl)pyrimidine | MS(M$^+$.): 216/218/220 |
| 26 | 4,6-dichloro-2-(cyclopropylmethyl)-5-methylpyrimidine | MS(MH$^+$): 217/219/221 |
| 27 | 4,6-dichloro-2-cyclobutyl-5-methylpyrimidine | MS(MH$^+$): 216/218/220 |
| 28 | 4,6-dichloro-2-cyclopropyl-5-nitropyrimidine | MS(M$^+$.): 233/235/237 |
| 29 | 4,6-dichloro-2-isopropyl-5-methylpyrimidine | MS(M$^+$.): 204/206/208 |
| 30 | 4,6-dichloro-2-cyclopentyl-5-methylpyrimidine | MS(M$^+$.): 230/232/234 |

EXAMPLE 4

Synthesis of Compounds of Formula II and II-A

4.1 Synthesis of 6-chloro-N,2-dicyclopropyl-5-fluoro-4-pyrimidinamine 31

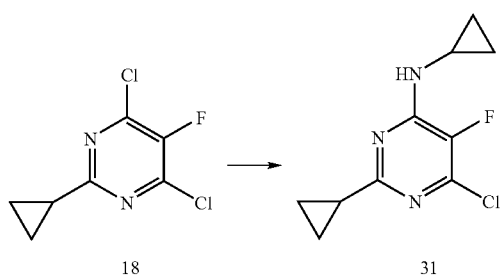

Cyclopropylamine (11.4 g, 0.200 mol) is added to 4,6-dichloro-2-cyclopropyl-5-fluoropyrimidine 18 (4.80 g, 23 mmol) and the solution is stirred at room temperature for 1 h. The mixture is diluted with diethylether, washed two times with a saturated sodium bicarbonate solution. The combined organic layers are dried over magnesium sulfate and concentrated in vacuo to afford 6-chloro-N,2-dicyclopropyl-5-fluoro-4-pyrimidinamine 31 as a yellow oil (4.99 g, 95%) which is used in the next step without further purification.

MS (M$^+$.): 227/229.

Compounds described in table 3 can be synthesized in an analogous way.

TABLE 3

| | | |
|---|---|---|
| 32 | 6-chloro-N,2-dicyclopropyl-4-pyrimidinamine | MS(MH+): 210/212 |
| 33 | 6-chloro-N,2-dicyclopropyl-5-methyl-4-pyrimidinamine | MS(MH+): 223/225 |
| 34 | 5,6-dichloro-N,2-dicyclopropyl-4-pyrimidinamine | MS(MH+): 244/246/248 |
| 35 | 6-chloro-N,2-dicyclopropyl-5-methoxy-4-pyrimidinamine | MS(MH+): 240/242 |
| 36 | 6-chloro-N,2-dicyclopropyl-5-ethyl-4-pyrimidinamine | MS(MH+): 238/240 |
| 37 | N-[6-chloro-2-(2-trans-methylcyclopropyl)-4-pyrimidinyl]-N-cyclopropylamine(i) | MS(MH+): 224/226 |
| 38 | N-[6-chloro-2-(2-trans-methylcyclopropyl)-4-pyrimidinyl]-N-cyclopropylamine | MS(MH+): 224/226<br>$[\alpha]_D^{25} = +87.28 (c = 1, CH_2Cl_2)$ |
| 39 | N-[6-chloro-2-(2-trans-methylcyclopropyl)-4-pyrimidinyl]-N-cyclopropylamine | MS(MH+): 224/226<br>$[\alpha]_D^{25} = -83.80 (c = 1, CH_2Cl_2)$ |
| 40 | 6-chloro-N-cyclopropyl-5-methyl-2-(2-trans-methylcyclopropyl)-4-pyrimidinamine | MS(MH+): 238/240 |
| 41 | 6-chloro-N-cyclopropyl-5-methyl-2-(2-cis-methylcyclopropyl)-4-pyrimidinamine | MS(MH+): 238/240 |
| 42 | N-[6-chloro-2-(cyclopropylmethyl)-5-methyl-4-pyrimidinyl]-N-cyclopropylamine | MS(MH+): 238/240 |
| 43 | 6-chloro-2-cyclobutyl-N-cyclopropyl-5-methyl-4-pyrimidinamine | MS(MH+): 237/239 |
| 44 | 6-chloro-N,2-dicyclopropyl-5-nitro-4-pyrimidinamine | MS(MH+): 255/257 |
| 45 | 6-chloro-N-cyclobutyl-2-cyclopropyl-5-methyl-4-pyrimidinamine | MS(MH+): 238/240 |
| 46 | 6-chloro-N-cyclopropyl-2-isopropyl-methyl-4-pyrimidinamine | MS(MH+): 226/228 |
| 47 | 6-chloro-2-cyclopentyl-N-cyclopropyl-5-methyl-4-pyrimidinamine | MS(MH+): 252/254 |
| 158 | 6-chloro-2-cyclopropyl-5-methyl-N-(2-methylcyclopropyl)-4-pyrimidinamine | MS(MH+): 238/240 |
| 159 | 6-chloro-2-cyclopropyl-5-methyl-N-(1-methylcyclopropyl)-4-pyrimidinamine | MS(MH+): 238/240 |
| 160 | 6-chloro-2-cyclopropyl-5-methyl-N-(2-phenylcyclopropyl)-4-pyrimidinamine | MS(MH+): 300/302 |

(i) compound 37 was resolved into its enantiomers 38 (first eluted) and 39 (second eluted) by chromatography on a chiral support (Daicel Chiralpak AD, isopropanol/n-hexane 1/99, 20° C.).

4.2 Synthesis of 4-chloro-2-cyclopropyl-6-(3-fluoro-azetidin-1-yl)-pyrimidine 163

4.2.1 Synthesis of 1-benzhydryl-3-fluoroazetidine 161

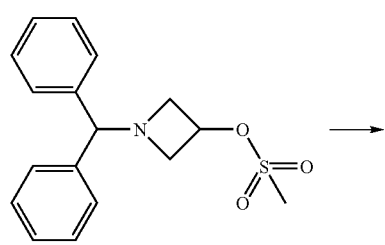

→

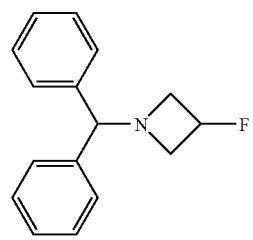

161

A solution of N-tetrabutylammonium fluoride (1 M solution in THF, 32 ml, 32 mmol) is added dropwise to a solution of methanesulfonic acid 1-benzhydryl-azetidin-3-yl ester (10.75 g, 32 mmol) in acetonitrile (250 ml). The solution is refluxed for 30 hours then concentrated in vacuo. The mixture is diluted with dichloromethane and washed two times with water. The combined organic layers are dried over magnesium sulfate and concentrated in vacuo to afford 10.5 g of a crude mixture which is purified by column chromatography (dichloromethane/hexane 3/1) to afford pure 1-benzhydryl-3-fluoroazetidine 161 (4.3 g, 55%).

MS (MH+): 242.

4.2.2 Synthesis of 3-fluoroazetidine Hydrochloride 162

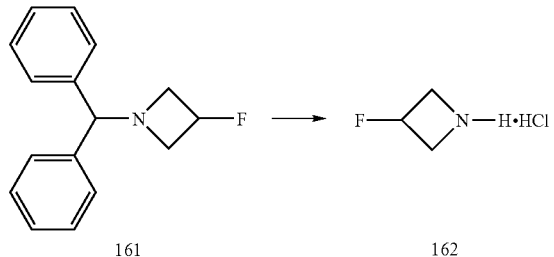

Palladium on barium sulfate (5%, 1.5 g) is suspended in methanol (20 ml) under a nitrogen atmosphere. 1-benzhydryl-3-fluoroazetidine 161 (4.3 g, 18 mmol) is added together with water (0.6 ml), methanol (80 ml) and a 3 N hydrochloric acid-methanol solution (16 ml). The mixture is put under a 50 psi hydrogen pressure and heated at 55° C. for 3 days. The catalyst is filtered and the filtrate is concentrated in vacuo. The mixture is diluted with water and washed three times with hexane. The combined aqueous layers are concentrated in vacuo to afford 3-fluoroazetidine hydrochloride 162 (2.1 g, 99%) which is used in the next step without further purification.

MS (MH+): 76.

Synthesis of 4-chloro-2-cyclopropyl-6-(3-fluoro-azetidin-1-yl)-pyrimidine 163

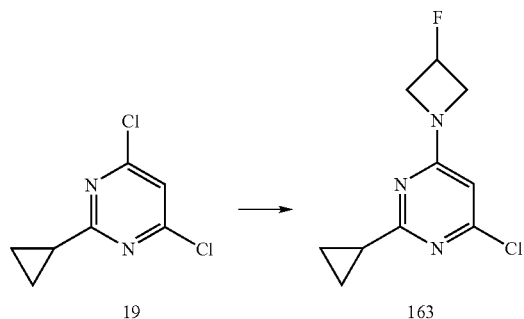

A mixture of 4,6-dichloro-2-cyclopropylpyrimidine 19 (1.05 g, 5.5 mmol), 3-fluoroazetidine hydrochloride 162 (0.68 g, 6 mmol) and potassium carbonate (2.48 g, 18 mmol) in 1-methoxy-2-propanol (10 ml) is heated at 65° C. for 2 hours. The mitre is cooled, concentrated in vacuo, diluted with dichloromethane and washed three times with water. The combined organic layers are dried over magnesium sulfate and concentrated in vacuo to afford 4-chloro-2-cyclopropyl-6-(3-fluoro-azetidin-1-yl)-pyrimidine 163 (1.16 g, 92%) as a yellow oil which is used in the next step without further purification.

MS (MH+): 228/230.

Compounds described in table 4 can be synthesized according to this method.

TABLE 4

| | IUPAC NAME | MS(LC-MS) |
|---|---|---|
| 164 | 4-(1-azetidinyl)-6-chloro-2-cyclopropyl-5-methylpyrimidine | 224/226 |
| 165 | 4-(1-azetidinyl)-6-chloro-2-cyclopropylpyrimidine | 210/212 |
| 166 | 4-chloro-2-cyclopropyl-5-methyl-6-(3-methyl-1-azetidinyl)pyrimidine | 238/240 |
| 167 | 4-chloro-2-cyclopropyl-6-(3-methyl-1-azetidinyl)pyrimidine | 224/226 |
| 168 | 4-chloro-2-cyclopropyl-6-(3,3-dimethyl-1-azetidinyl)-5-methylpyrimidine | 252/254 |
| 169 | 1-(6-chloro-2-cyclopropyl-5-methyl-4-pyrimidinyl)-3-azetidinol | 240/242 |
| 170 | 4-chloro-2-cyclopropyl-6-(3-fluoro-1-azetidinyl)-5-methylpyrimidine | 242/244 |
| 171 | 4-chloro-2-cyclopropyl-6-(3-methoxy-1-azetidinyl)-5-methylpyrimidine | 254/256 |

EXAMPLE 5

Synthesis of 4-hydroxypyrimidines of Formula XII

5.1 Synthesis of 2-cyclopropyl-6,7-dihydro-5H-pyrrolo[2,3-d]pyrimidin-4-ol 48

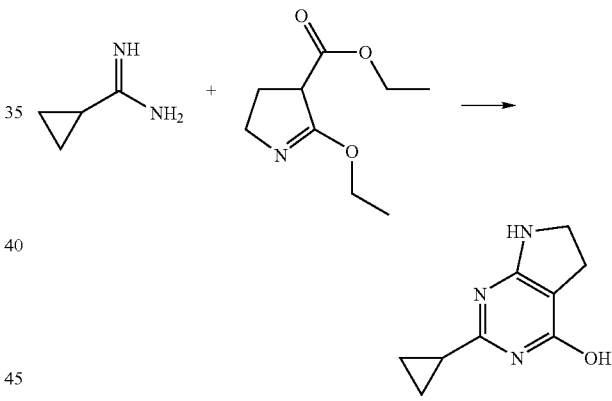

Sodium (0.417 g, 18.1 mmol) is dissolved in methanol (65 ml) under a nitrogen atmosphere. Cyclopropanecarboximidamide hydrochloride (2.19 g, 18.1 mmol) is added in one portion. The mixture is stirred at room temperature for 0.25 h, then filtered upon hyflocel. The filtrate is concentrated in vacuo to 30 ml. This free base is added to a solution of sodium (0.834 g, 36.2 mmol) in methanol (130 ml) under a nitrogen atmosphere, at room temperature. 2-ethoxy-4,5-dihydro-3H-pyrrole-3-carboxylic acid ethyl ester (3.4 g, 18.1 mmol) in methanol is added and the mire is stirred at 60° C. overnight. After cooling, the solvent is evaporated and the solid obtained is dissolved in water. The pH is adjusted at 5 with a 5 N HCl solution and the white precipitate formed is filtered and dried. 2-cyclopropyl-6,7-dihydro-5H-pyrrolo[2,3-d]pyrimidin-4-ol 48 (1.88 g, 59%) is obtained as a white powder and used in the next step without further purification.

MS (MH+): 178.

EXAMPLE 6

Synthesis of 4-chloropyrimidines of Formula X 6.1 Synthesis of 4-chloro-2-cyclopropyl-5,6,7,8-tetrahydro-5H-pyrido[2,3-d]pyrimidine 50

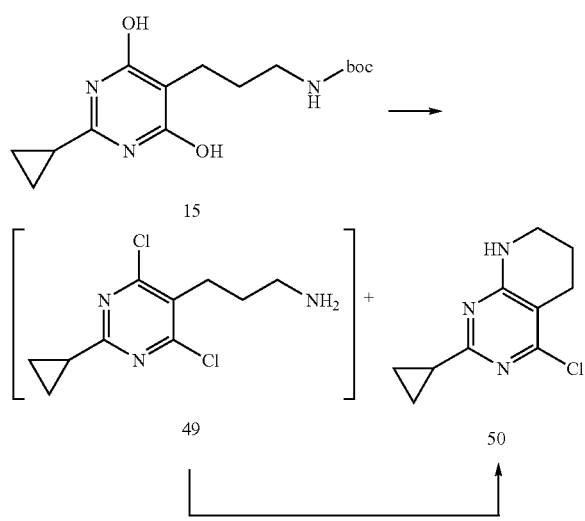

[3-(2-cyclopropyl-4,6-dihydroxy-pyrimidin-5-yl)-propyl]-carbamic acid tert-butyl ester 15 (1.4 g, 4.5 mmol) is suspended in phosphorus oxychloride (10 ml). A mixture of N,N-diethylaniline (0.744 g, 5 mmol) and phosphorus oxychloride (10 ml) is added dropwise to the suspension at room temperature. The resulting mixture is stirred at 100° C. overnight. The solution is poured onto crushed ice and extracted two times with dichloromethane. The aqueous layer is alkalinized using a saturated sodium hydrogenocarbonate solution (pH 8), extracted two times with dichloromethane, reacidified using HCl 5N (pH 3) and extracted again with dichloromethane. The combined aqueous layers are alkalinized (pH 10) and the white precipitate formed is filtered and dried. The combined organic layers are dried over magnesium sulfate and concentrated in vacuo to afford a mixture of 4-chloro-2-cyclopropyl-5,6,7,8-tetrahydro-5H-pyrido[2,3-d]pyrimidine 50 and non-cyclized 3-(4,6-dichloro-2-cyclopropyl-pyrimidin-5-yl)propylamine 49. This mixture is dissolved in 1-methoxy-2-propanol and heated at 140° C. for 5 h. After cooling, the solution is diluted with dichloromethane and washed with water (2×) and with an hydrochloric acid solution (1 N). The combined organic layers are dried over magnesium sulfate and concentrated in vacuo. The resulting crude mixture is purified by chromatography on silica gel preparative plates (dichloromethane/ethanol/ammonia 97/3/0.3) to afford a solid, which is combined with the first-formed precipitate. Pure 4-chloro-2-cyclopropyl-5,6,7,8-tetrahydro-5H-pyrido[2,3-d]pyrimidine 50 is obtained as an orange solid (209 mg, 20%).

MS (MH⁺): 210/212.

4-chloro-2-cyclopropyl-6,7,8,9-tetrahydro-5H-pyrimido[4,5-b]azepine 51 can be synthesized in an analogous way.

MS (MH⁺): 224/226

6.2 Synthesis of 4-chloro-2-cyclopropyl-6,7-dihydro-5H-pyrrolo[2,3-d]pyrimidine 52

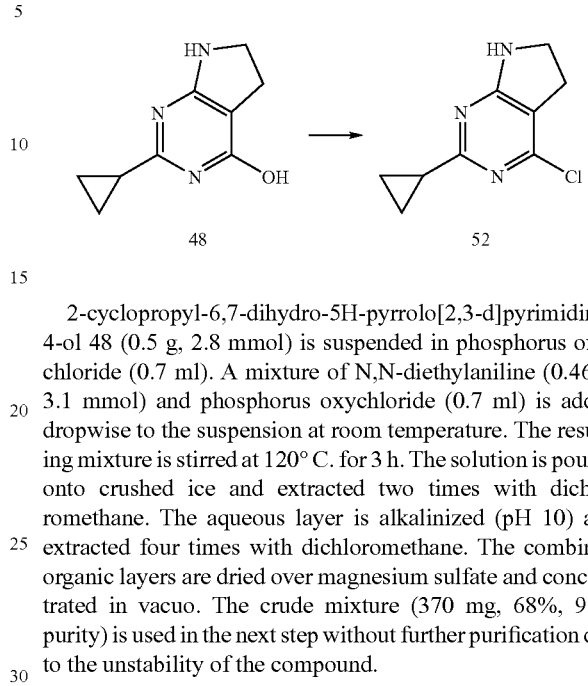

2-cyclopropyl-6,7-dihydro-5H-pyrrolo[2,3-d]pyrimidin-4-ol 48 (0.5 g, 2.8 mmol) is suspended in phosphorus oxychloride (0.7 ml). A mixture of N,N-diethylaniline (0.46 g, 3.1 mmol) and phosphorus oxychloride (0.7 ml) is added dropwise to the suspension at room temperature. The resulting mixture is stirred at 120° C. for 3 h. The solution is poured onto crushed ice and extracted two times with dichloromethane. The aqueous layer is alkalinized (pH 10) and extracted four times with dichloromethane. The combined organic layers are dried over magnesium sulfate and concentrated in vacuo. The crude mixture (370 mg, 68%, 91% purity) is used in the next step without further purification due to the instability of the compound.

MS (MH⁺): 196/198

EXAMPLE 7

Synthesis of Compounds of Formula I 7.1 Synthesis of N,2-dicyclopropyl-5-fluoro-6-(4-thiomorpholinyl)-4-pyrimidinamine 120

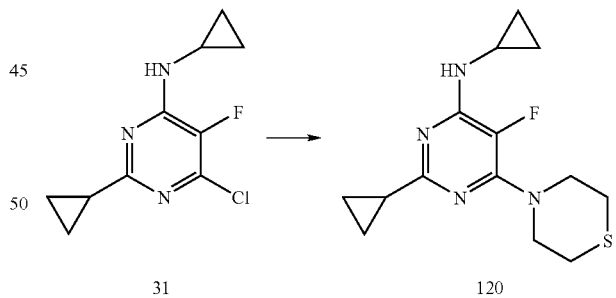

A mixture of thiomorpholine (2.27 g, 22 mmol) and 6-chloro-N,2-dicyclopropyl-5-fluoro-4-pyrimidinamine 31 (1 g, 4.4 mmol) is stirred at 110° C. for 18 hours. After cooling, the brown solution is diluted with dichloromethane, washed two times with a saturated sodium bicarbonate solution. The combined organic layers are dried over magnesium sulfate and concentrated under high vacuum to afford a brown oil. The crude oil is purified by column chromatography (hexane/ethyl acetate: 80/20) to give N,2-dicyclopropyl-5-fluoro-6-(4-thiomorpholinyl)-4-pyrimidinamine 120 (915 mg, 71%) as a yellowish solid.

7.2 Synthesis of $N^4$-cyclohexyl-$N^6$,2-dicyclopropyl-5-methyl-4,6-pyrimidinediamine 141

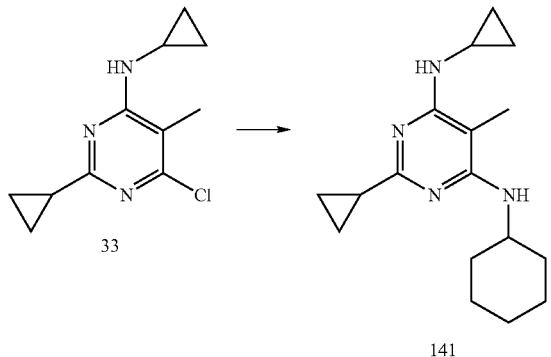

A mixture of cyclohexylamine (1.78 g, 18 mmol) and 6-chloro-N,2-dicyclopropyl-5-methyl-4-pyrimidinamine 33 (0.70 g, 3 mmol) in 1-methoxy-2-propanol (2 ml) is stirred at 125° C. for 120 hours. After cooling, the brown solution is diluted with dichloromethane, washed two times with a saturated sodium bicarbonate solution. The combined organic layers are dried over magnesium sulfate and concentrated under high vacuum to afford a brown oil. The crude oil is purified by column chromatography (dichloromethane/methanol: 97.3/2.7) to give pure $N^4$-cyclohexyl-$N^6$,2-dicyclopropyl-5-methyl-4,6-pyrimidinediamine 141 (0.150 g, 17%).

7.3 Synthesis of 6-(1-azepanyl)-$N^4$,2-dicyclopropyl-4,5-pyrimidinediamine 63

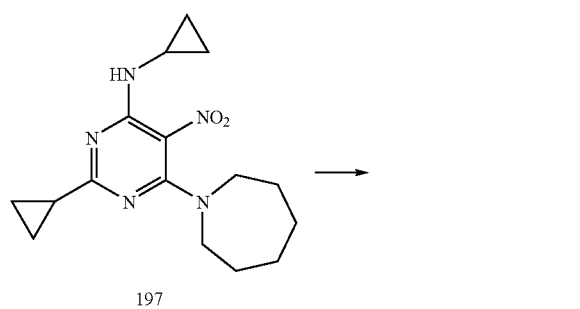

6-(1-azepanyl)-N,2-dicyclopropyl-5-nitro-4-pyrimidinamine 197 was synthesized as described in 7.1 using 6-chloro-N,2-dicyclopropyl-5-nitro-4-pyrimidinamine 44 and azepane as starting material.

MS (MH$^+$): 318.

To a suspension of 6-(1-azepanyl)-N,2-dicyclopropyl-5-nitro-4-pyrimidinamine 197 (0.5 g, 16 mmol) in 1,4-dioxane (35 ml) and water (35 ml) is added sodium hydrosulfite (2.19 g, 13 mmol) and ammonia (25% solution, 1.2 ml). The mixture is stirred at room temperature for 10 h then diluted with ethyl acetate and washed three times with water. The combined organic layers are dried over magnesium sulfate and concentrated in vacuo to afford a yellow oil. The crude oil is purified by column chromatography (dichloromethane/ethanol/ammonia: 95/5/0.5) to give pure 6-(1-azepanyl)-$N^4$,2-dicyclopropyl-4,5-pyrimidinediamine 63 (137 mg, 30%) as a reddish solid.

7.4 Synthesis of 1-[2-cyclopropyl-6-(cyclopropylamino)-5-methyl-4-pyrimidinyl]-4-piperidinone Hydrate 107

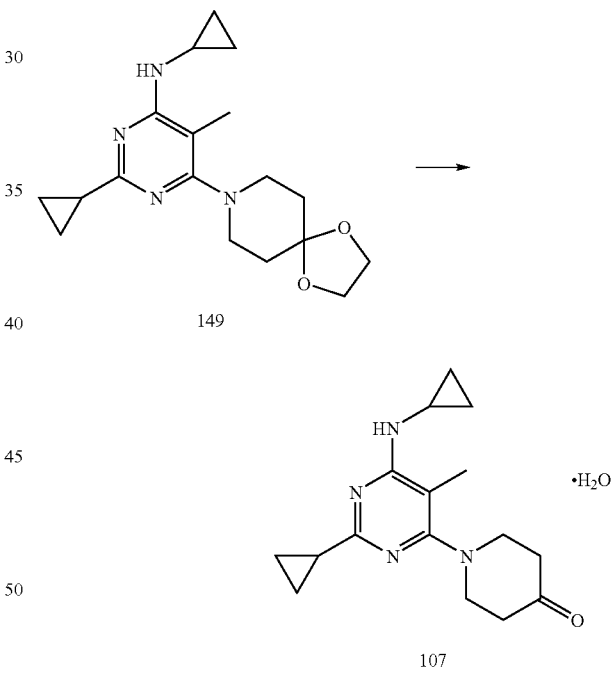

A solution of 1 N HCl (15 ml) is added to a solution of N,2-dicyclopropyl-6-(1,4-dioxa-8-azaspiro[4.5]dec-8-yl)-5-methyl-4-pyrimidinamine 149 (285 mg, 0.86 mmol) in tetrahydrofuran (15 ml). The mixture is stirred at room temperature for 18 h, then diluted with dichloromethane and washed three times with sodium bicarbonate. The combined organic layers are dried over magnesium sulfate and concentrated in vacuo to afford a white paste. The compound is dried under vacuum to give pure 1-[2-cyclopropyl-6-(cyclopropylamino)-5-methyl-4-pyrimidinyl]-4-piperidinone hydrate 107 (160 mg, 61%) as a white paste.

7.5 Synthesis of 6-azepan-1-yl-5-bromo-N,2-dicyclopropylpyrimidin-4-amine 61

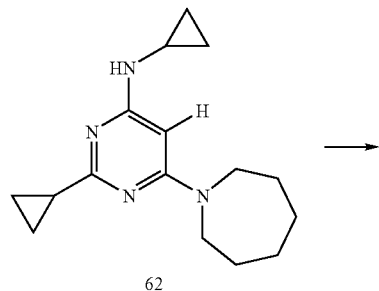

62

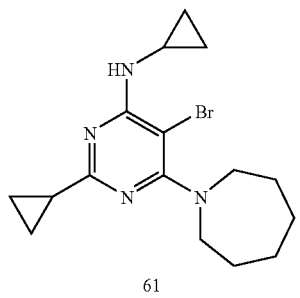

61

N-Bromosuccinimide (0.39 g, 2.2 mmol) is added to a solution of 6-(1-azepanyl)-N,2-dicyclopropyl-4-pyrimidinamine 62 (0.5 g, 1.84 mmol) in chloroform (2 ml). The mixture is stirred at 60° C. overnight then cooled, diluted with dichloromethane and washed two times with water. The combined organic layers are dried over magnesium sulfate and concentrated in vacuo. The crude mixture is purified by column chromatography (dichloromethane/ethanol: 97/3) to give pure 6-azepan-1-yl-5-bromo-N,2-dicyclopropylpyrimidin-4-amine 61 (134 mg, 21%) as a brownish paste.

7.6 Synthesis of 4-azepan-1-yl-2-cyclopropyl-5,6,7,8-tetrahydro-pyrido[2,3-d]pyrimidine 155

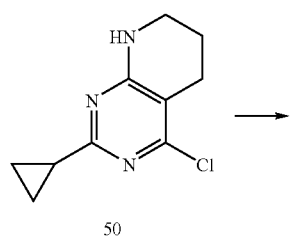

50

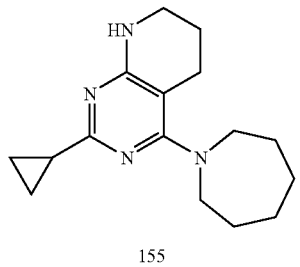

155

A mixture of azepane (18.2 ml, 142 mmol) and 4-chloro-2-cyclopropyl-5,6,7,8-tetrahydro-5H-pyrido[2,3-]pyrimidine 50 (0.851 g, 4.06 mmol) is stirred four days at 110° C. After cooling, the brown solution is diluted with dichloromethane and washed two times with water. The combined organic layers are dried over magnesium sulfate and concentrated under high vacuum to afford a brown oil. The crude oil is purified by column chromatography (dichloromethane/ethanol/ammonia: 90/10/1) to give pure 4-azepan-1-yl-2-cyclopropyl-5,6,7,8-tetrahydro-pyrido[2,3-d]pyrimidine 155 as a brown solid.

7.7 Synthesis of 1-[2-cyclopropyl-6-(3-fluoro-azetidin-1-yl)-pyrimidin-4-yl]azepane Fumarate (3:2) 195

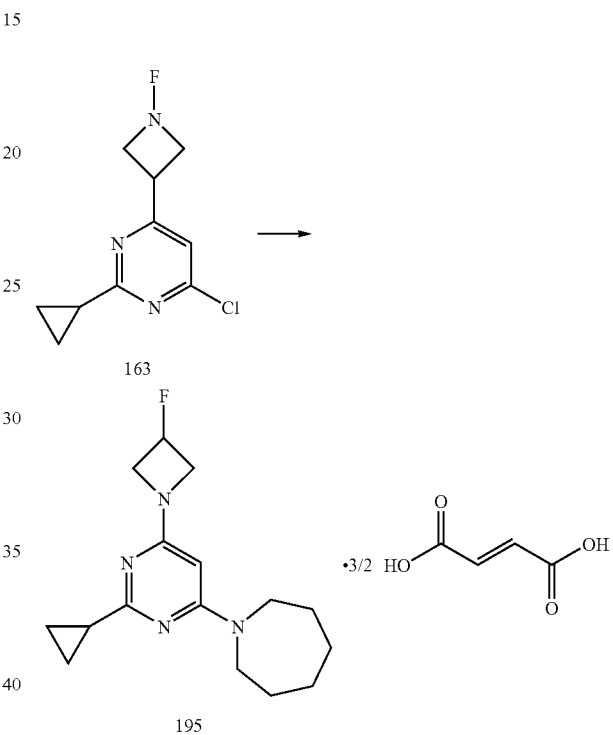

A mixture of hexamethyleneimine (2.87 g, 29 mmol) and 4-chloro-2-cyclopropyl-6-(3-fluoro-azetidin-1-yl)-pyrimidine 163 (1.1 g, 4.8 mmol) in 1-methoxy-2-propanol (2 ml) is stirred at 110° C. for 6 hours. After cooling, the solution is diluted with dichloromethane, washed two times with a saturated sodium bicarbonate solution. The combined organic layers are dried over magnesium sulfate and concentrated under high vacuum to afford a brown oil (2.15 g). The crude oil is purified by column chromatography (dichloromethane/methanol 99.5/0.5) to give pure 1-[2-cyclopropyl-6-(3-fluoro-azetidin-1-yl)-pyrimidin-4-yl]azepane (1 g, 72%).

MS (MH$^+$): 291.

A solution of fumaric acid (0.6 g) in isopropanol (4 ml) is added to a solution of 1-[2-cyclopropyl-6-(3-fluoro-azetidin-1-yl)-pyrimidin-4-yl]azepane in diisopropyl ether (10 ml). The mixture is triturated, then filtered, recrystallized from diisopropyl ether and dried in vacuo to afford pure 1-[2-cyclopropyl-6-(3-fluoro-azetidin-1-yl)-pyrimidin-4-yl]azepane fumarate (3:2) 195 (1.2 g, 58%).

MS (MH$^+$): 291.

7.8 Synthesis of Methanesulfonic Acid 1-(6-azepan-1-yl-2-cyclopropyl-5-methyl-pyrimidin-4-yl)-azetidin-3-yl Ester 190

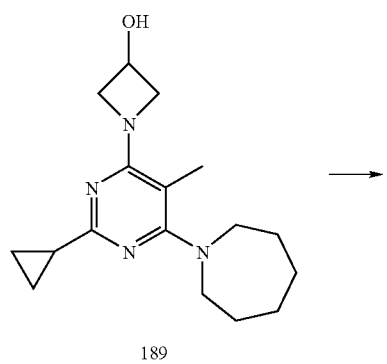

189

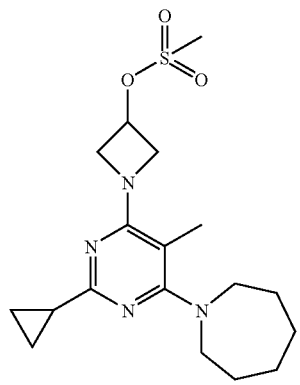

190

A solution of methanesulfonyl chloride (0.63 ml, 7.6 mmol) in dichloromethane (10 ml) is added dropwise to a solution of 1-(6-azepan-1-yl-2-cyclopropyl-5-methyl-pyrimidin-4-yl)-azetidin-3-ol 189 (1.90 g, 6.3 mmol) and triethylamine (1.74 ml, 13 mmol) in dichloromethane (90 ml) at 0° C. The mixture is stirred 1 hour at 0° C. and 1 hour at room temperature. Water (40 ml) is added and the mixture is extracted three times with dichloromethane. The combined organic layers are dried over magnesium sulfate and concentrated in vacuo to afford pure methanesulfonic acid 1-(6-azepan-1-yl-2-cyclopropyl-5-methyl-pyrimidin-4-yl)-azetidin-3-yl ester 190 (2.66 g, 100%).

MS (MH$^+$): 381.

7.9 Synthesis of 1-[6-(3-bromo-azetidin-1-yl)-2-cyclopropyl-5-methyl-pyrimidin-4-yl]-azepane 182

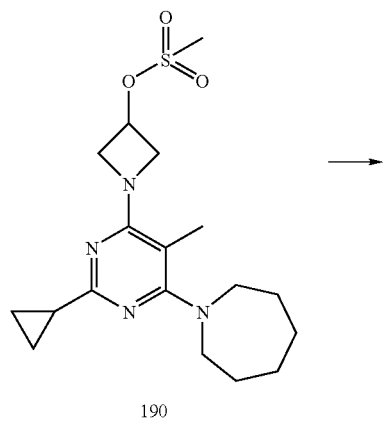

190

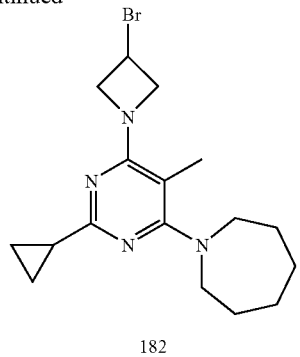

182

A mixture of methanesulfonic acid 1-(6-azepan-1-yl-2-cyclopropyl-5-methyl-pyridin-4-yl)-azetidin-3-yl ester 190 (0.4 g, 1 mmol) and sodium bromide (0.103 g, 1 mmol) in N,N-dimethylformamide (10 ml) is heated at 100° C. for 6 days. The mixture is then cooled and concentrated in vacuo. The mixture is diluted with dichloromethane and washed two times with water. The combined organic layers are dried over magnesium sulfate and concentrated in vacuo to afford 0.4 g of a crude mixture, which is purified by column chromatography (dichloromethane/methanol 98/2). 1-[6-(3-bromo-azetidin-1-yl)-2-cyclopropyl-5-methyl-pyrimidin-4-yl]-azepane 182 (0.11 g, 30%) is obtained.

MS (MH$^+$): 365/367.

7.10 Synthesis of 1-[6-azepan-1-yl-2-cyclopropyl-5-methyl-pyrimidin-4-yl]-azetidine-3-carbonitrile 183

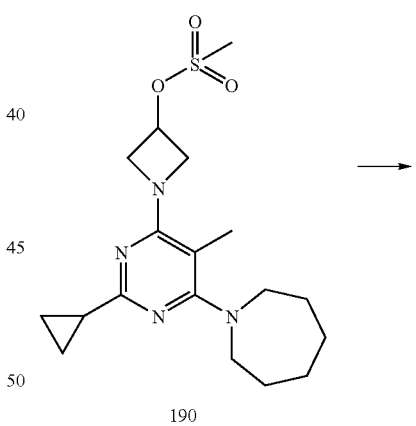

190

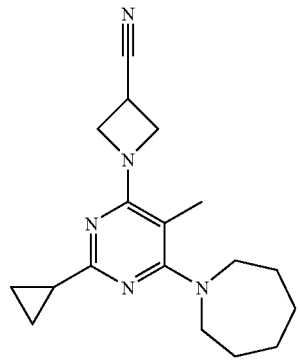

183

A mixture of methanesulfonic acid 1-(6-azepan-1-yl-2-cyclopropyl-5-methyl-pyrimidin-4-yl)-azetidin-3-yl ester 190 (0.3 g, 0.8 mmol) and sodium cyanide (0.047 g, 1.0 mmol) in N,N-dimethylformamide (5 ml) is heated at 120° C. for 24 hours. The mixture is then cooled and concentrated in vacuo. The mixture is diluted with dichloromethane and washed two times with water. The combined organic layers are dried over magnesium sulfate and concentrated in vacuo to afford 0.4 g of a crude mixture, which is purified by column chromatography (dichloromethane/ethanol 98/2). 0.10 g (60%) of 1-(6-azepan-1-yl-2-cyclopropyl-5-methyl-pyrimidin-4-yl]-azetidine-3-carbonitrile 183 is obtained.

MS (MH$^+$): 312.

7.11 Synthesis of 1-(6-azepany-1-yl-2-cyclopropyl-5-methyl-pyrimidin-4-yl)-azetidin-3-one 193

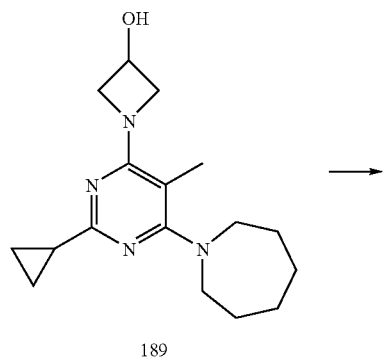

189

→

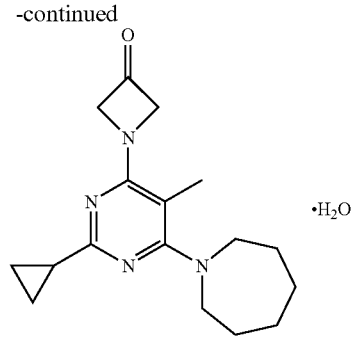

193

A solution of sulfur trioxide/pyridine complex (1.4 g, 8.8 mmol) in DMSO (3.5 ml) is added dropwise to a solution of 1-(6-azepany-1-yl-2-cyclopropyl-5-methyl-pyrimidin-4-yl)-azetidin-3-ol 189 (0.3 g, 0.7 mmol) and triethylamine (1 ml) in DMSO (7 ml). The mixture is stirred at room temperature for 24 hours, poured onto ice, diluted with ethyl acetate and washed two times with water. The combined organic layers are dried over magnesium sulfate and concentrated in vacuo to afford 0.4 g (96%) of pure 1-(6-azepany-1-yl-2-cyclopropyl-5-methyl-pyrimidin-4-yl)-azetidin-3-one hydrate 193.

MS (MH$^+$): 319.

Compounds described in table 5 can be synthesized according to one of these methods.

TABLE 5

| | Salt/solvate | Configuration data | | | Free base IUPAC NAME | MH$^+$ (M$^{+\cdot}$) | DSC ° C. (mp) | $alpha_D$ |
|---|---|---|---|---|---|---|---|---|
| 53 | 1 HCl | | achiral | | N,2-dicyclopropyl-6-(1,3-thiazolidin-3-yl)-4-pyrimidinamine | (262) | 181.3 | |
| 54 | 1 HCl | | achiral | | N-cyclopropyl-2-isopropyl-6-(1,3-thiazolidin-3-yl)-4-pyrimidinamine | (264) | 204.4 | |
| 55 | 1 maleate | | achiral | | 6-(1-azepanyl)-2-cyclobutyl-N-cyclopropyl-5-methyl-4-pyrimidinamine | 301 | | |
| 56 | 1 maleate | | achiral | | 6-(1-azepanyl)-N,2-dicyclopropyl-5-methyl-4-pyrimidinamine | 287 | | |
| 57 | ½ fumarate | | achiral | | 6-(1-azepanyl)-N,2-dicyclopropyl-5-methyl-4-pyrimidinamine | 287 | 149.9 | |
| 58 | 1 maleate | | achiral | | 6-(1-azepanyl)-N-cyclobutyl-2-cyclopropyl-5-methyl-4-pyrimidinamine | 301 | | |
| 59 | 1 maleate | | achiral | | 6-(1-azepanyl)-5-chloro-N,2-dicyclopropyl-4-pyrimidinamine | 307 | 85.2 | |
| 60 | 1 maleate | | achiral | | 6-(1-azepanyl)-N,2-dicyclopropyl-5-fluoro-4-pyrimidinamine | 291 | 111.2 | |
| 61 | | | achiral | | 6-azepan-1-yl-5-bromo-N,2-dicyclopropyl-4-pyrimidinamine | 351/353 | | |
| 62 | | | achiral | | 6-(1-azepanyl)-N,2-dicyclopropyl-4-pyrimidinamine | 273 | 124.6 | |
| 63 | | | achiral | | 6-(1-azepanyl)-N$^4$,2-dicyclopropyl-4,5-pyrimidinediamine | 288 | (76.9) | |
| 64 | 1 maleate | | achiral | | 6-(1-azepanyl)-N-cyclopropyl-2-isopropyl-5-methyl-4-pyrimidinamine | 289 | | |
| 65 | 1 maleate | A-1,2 | rac | trans | 6-(1-azepanyl)-N-cyclopropyl-5-methyl-2-(2-methylcyclopropyl)-4-pyrimidinamine | 301 | | |
| 66 | 1 maleate | B-1,2 | rac | cis | 6-(1-azepanyl)-N-cyclopropyl-5-methyl-2-(2-methylcyclopropyl)-4-pyrimidinamine | 301 | | |
| 67 | | B-1§,2§ | pure | trans | 6-(1-azepanyl)-N-cyclopropyl-5-methyl-2-(2-methylcyclopropyl)-4-pyrimidinamine | 301 | | −58.79 |
| 68 | | A-1§,2§ | pure | trans | 6-(1-azepanyl)-N-cyclopropyl-5-methyl-2-(2-methylcyclopropyl)-4-pyrimidinamine | 301 | | +57.65 |
| 69 | 1 maleate | | achiral | | 6-(1-azepanyl)-N-cyclopropyl-2-(cyclopropylmethyl)-5-methyl-4-pyrimidinamine | 301 | | |
| 70 | | A-1,2 | rac | trans | 6-(1-azepanyl)-5-chloro-N-cyclopropyl-2-(2-methylcyclopropyl)-4-pyrimidinamine | 321 | | |
| 71 | | A-1,2 | rac | trans | 6-(1-azepanyl)-N-cyclopropyl-2-(2-methylcyclopropyl)-4-pyrimidinamine | 287 | | |
| 72 | 0.2 iPrOH, 1 maleate | | achiral | | 6-(1-azocanyl)-N,2-dicyclopropyl-5-methyl-4-pyrimidinamine | 301 | | |

TABLE 5-continued

| | Salt/solvate | Configuration data | | | Free base IUPAC NAME | MH+ (M+·) | DSC °C. (mp) | alphaD |
|---|---|---|---|---|---|---|---|---|
| 73 | | A-1,2 | rac | trans | 6-(1-azocanyl)-N-cyclopropyl-2-(2-methylcyclopropyl)-4-pyrimidinamine | 301 | 108.5 | |
| 74 | | 3,5 | mixt | | N,2-dicyclopropyl-6-(3,5-dimethyl-1-piperidinyl)-5-methyl-4-pyrimidinamine | 301 | 91.2 | |
| 75 | 1 maleate | | achiral | | N,2-dicyclopropyl-6-[4-(2-methoxyphenyl)-1-piperidinyl]-5-methyl-4-pyrimidinamine | 379 | 123.6 | |
| 76 | 1 iPrOH, 1 maleate | | achiral | | {1-[2-cyclopropyl-6-(cyclopropylamino)-5-methyl-4-pyrimidinyl]-4-piperidinyl}(diphenyl)methanol | 455 | 86.1 | |
| 77 | | | achiral | | N,2-dicyclopropyl-5-methyl-6-[4-(trifluoromethyl)piperidin-1-yl]-4-pyrimidinamine | 341 | (86.4) | |
| 78 | 1 maleate | | achiral | | N,2-dicyclopropyl-6-(4,4-difluoro-1-piperidinyl)-5-methyl-4-pyrimidinamine | 309 | 121.9 | |
| 79 | | | achiral | | N,2-dicyclopropyl-6-(4,4-dimethyl-1-piperidinyl)-5-methyl-4-pyrimidinamine | 301 | | |
| 80 | 1 HCl | | achiral | | N,2-dicyclopropyl-6-(4,4-dimethyl-1-piperidinyl)-5-methyl-4-pyrimidinamine | 301 | | |
| 81 | | | achiral | | 1-[2-cyclopropyl-6-(cyclopropylamino)-5-methyl-4-pyrimidinyl]-4-piperidinecarboxamide | 316 | 230.6 | |
| 82 | 1 maleate | | achiral | | 6-(4-benzyl-1-piperidinyl)-N,2-dicyclopropyl-5-methyl-4-pyrimidinamine | 363 | 132.1 | |
| 83 | | | achiral | | 1-[2-cyclopropyl-6-(cyclopropylamino)-5-methyl-4-pyrimidinyl]-4-piperidinecarboxylic acid | 317 | 219.6 | |
| 84 | | | achiral | | 1-[2-cyclopropyl-6-(cyclopropylamino)-5-methyl-4-pyrimidinyl]-4-phenyl-4-piperidinecarbonitrile | 374 | 145.3 | |
| 85 | 1 maleate | | achiral | | ethyl 1-[2-cyclopropyl-6-(cyclopropylamino)-5-methyl-4-pyrimidinyl]-4-piperidinecarboxylate | 345 | 118.9 | |
| 86 | | | achiral | | N,2-dicyclopropyl-6-(4-ethyl-1-piperidinyl)-5-methyl-4-pyrimidinamine | 301 | | |
| 87 | 1 HCl | | achiral | | N,2-dicyclopropyl-6-(4-ethyl-1-piperidinyl)-5-methyl-4-pyrimidinamine | 301 | | |
| 88 | | | achiral | | N,2-dicyclopropyl-6-(4-ethyl-4-methyl-1-piperidinyl)-5-methyl-4-pyrimidinamine | 315 | | |
| 89 | 1 HCl | | achiral | | N,2-dicyclopropyl-6-(4-ethyl-4-methyl-1-piperidinyl)-5-methyl-4-pyrimidinamine | 315 | | |
| 90 | | | achiral | | 1-[2-cyclopropyl-6-(cyclopropylamino)-5-methyl-4-pyrimidinyl]-4-piperidinol | 289 | 150.0 | |
| 91 | | | achiral | | 1-[2-cyclopropyl-6-(cyclopropylamino)-5-methyl-4-pyrimidinyl]-4-phenyl-4-piperidinol | 365 | | |
| 92 | | | achiral | | 1-[2-cyclopropyl-6-(cyclopropylamino)-5-fluoro-4-pyrimidinyl]-4-phenyl-4-piperidinol | 369 | | |
| 93 | | | achiral | | {1-[2-cyclopropyl-6-(cyclopropylamino)-5-methyl-4-pyrimidinyl]-4-piperidinyl}methanol | 303 | 113.9 | |
| 94 | 1 maleate | | achiral | | N,2-dicyclopropyl-5-ethyl-6-(4-methyl-1-piperidinyl)-4-pyrimidinamine | 301 | | |
| 95 | 1 maleate | | achiral | | N,2-dicyclopropyl-5-methyl-6-(4-methyl-1-piperidinyl)-4-pyrimidinamine | 287 | 97.9 | |
| 96 | | | achiral | | N,2-dicyclopropyl-5-fluoro-6-(4-methyl-1-piperidinyl)-4-pyrimidinamine | 291 | | |
| 97 | | A-1,2 | rac | trans | N-cyclopropyl-5-methyl-2-(2-methylcyclopropyl)-6-(4-methyl-1-piperidinyl)-4-pyrimidinamine | 301 | 91.3 | |
| 98 | 1 maleate | B-1,2 | rac | cis | N-cyclopropyl-5-methyl-2-(2-methylcyclopropyl)-6-(4-methyl-1-piperidinyl)-4-pyrimidinamine | 301 | | |
| 99 | | A-1§,2§ | pure | trans | N-cyclopropyl-5-methyl-2-(2-methylcyclopropyl)-6-(4-methyl-1-piperidinyl)-4-pyrimidinamine | 301 | | 61.65 |
| 100 | | B-1§,2§ | pure | trans | N-cyclopropyl-5-methyl-2-(2-methylcyclopropyl)-6-(4-methyl-1-piperidinyl)-4-pyrimidinamine | 301 | | −63.51 |
| 101 | | A-1,2 | rac | trans | N-cyclopropyl-2-(2-methylcyclopropyl)-6-(4-methyl-1-piperidinyl)-4-pyrimidinamine | 287 | 120.3 | |
| 102 | 1 HCl | A-1,2 | rac | trans | N-cyclopropyl-2-(2-methylcyclopropyl)-6-(4-methyl-1-piperidinyl)-4-pyrimidinamine | 287 | 148.1 | |
| 103 | 1 maleate | A-1,2 | rac | trans | N-cyclopropyl-2-(2-methylcyclopropyl)-6-(4-methyl-1-piperidinyl)-4-pyrimidinamine | 287 | 132.1 | |
| 104 | | A-1§,2§ | pure | trans | N-cyclopropyl-2-(2-methylcyclopropyl)-6-(4-methyl-1-piperidinyl)-4-pyrimidinamine | 287 | | 65.61 |
| 105 | | B-1§,2§ | pure | trans | N-cyclopropyl-2-(2-methylcyclopropyl)-6-(4-methyl-1-piperidinyl)-4-pyrimidinamine | 287 | | −70.6 |
| 106 | 1 HCl | | achiral | | N,2-dicyclopropyl-5-methyl-6-(4-methylene-1-piperidinyl)-4-pyrimidinamine | 285 | | |
| 107 | 1 H$_2$O | | achiral | | 1-[2-cyclopropyl-6-(cyclopropylamino)-5-methyl-4-pyrimidinyl]-4-piperidinone | 305 | | |
| 108 | | | achiral | | N$^4$,2-dicyclopropyl-N$^6$,5-dimethyl-N$^6$-[2-(2-thienyl)ethyl]-4,6-pyrimidinediamine | 329 | | |
| 109 | 1 maleate | | achiral | | N$^4$,2-dicyclopropyl-5-methyl-N$^6$-[2-(2-thienyl)ethyl]-4,6-pyrimidinediamine | 315 | 129.1 | |
| 110 | 1 maleate | | achiral | | N$^4$,2-dicyclopropyl-N$^6$-(2-furylmethyl-N$^6$,5-dimethyl-4,6-pyrimidinediamine | 299 | | |

TABLE 5-continued

| | Salt/solvate | Configuration data | | Free base IUPAC NAME | MH+ (M+·) | DSC °C. (mp) | alphaD |
|---|---|---|---|---|---|---|---|
| 111 | 1 maleate | achiral | | $N^4$,2-dicyclopropyl-5-methyl-$N^6$-(2-thienylmethyl)-4,6-pyrimidinediamine | 301 | 151.9 | |
| 112 | 1 maleate | achiral | | N,2-dicyclopropyl-6-(3,6-dihydro-1(2H)-pyridinyl)-5-methyl-4-pyrimidinamine | 271 | 118.9 | |
| 113 | | A-1,2 | rac trans | N-cyclopropyl-6-(3,6-dihydro-1(2H)-pyridinyl)-2-(2-methylcyclopropyl)-4-pyrimidinamine | 271 | 107.4 | |
| 114 | 1 HCl | A-1,2 | rac trans | N-cyclopropyl-6-(3,6-dihydro-1(2H)-pyridinyl)-2-(2-methylcyclopropyl)-4-pyrimidinamine | 271 | | |
| 115 | 1 maleate | achiral | | 6-(3-azabicyclo[3.2.1]oct-3-yl)-N,2-dicyclopropyl-5-methyl-4-pyrimidinamine | 299 | | |
| 116 | 1 maleate | achiral | | $N^4$,2-dicyclopropyl-5-methyl-$N^6$-(4-pyridinylmethyl)-4,6-pyrimidinediamine | 296 | 165.3 | |
| 117 | 2 maleate | A-1,2 | rac trans | $N^4$-cyclopropyl-2-(2-methylcyclopropyl)-$N^6$-(4-pyridinylmethyl)-4,6-pyrimidinediamine | 296 | | |
| 118 | 1 maleate | achiral | | N,2-dicyclopropyl-5-ethyl-6-(4-thiomorpholinyl)-4-pyrimidinamine (1:1) | 305 | 99.5 | |
| 119 | 1 HCl | achiral | | N,2-dicyclopropyl-5-methyl-6-(4-thiomorpholinyl)-4-pyrimidinamine | (290) | 224.4 | |
| 120 | | achiral | | N,2-dicyclopropyl-5-fluoro-6-(4-thiomorpholinyl)-4-pyrimidinamine | 295 | (87) | |
| 121 | | achiral | | N,2-dicyclopropyl-6-(4-thiomorpholinyl)-4-pyrimidinamine | (276) | | |
| 122 | | achiral | | N,2-dicyclopropyl-5-methoxy-6-(4-thiomorpholinyl)-4-pyrimidinamine | 307 | | |
| 123 | 1 maleate | achiral | | N-cyclopropyl-2-isopropyl-5-methyl-6-(4-thiomorpholinyl)-4-pyrimidinamine | 293 | 89.64 | |
| 124 | 1 HCl | A-1§,2§ | pure trans | N-cyclopropyl-5-methyl-2-(2-methylcyclopropyl)-6-(4-thiomorpholinyl)-4-pyrimidinamine | (304) | | +48.7 |
| 125 | 1 HCl | B-1§,2§ | pure trans | N-cyclopropyl-5-methyl-2-(2-methylcyclopropyl)-6-(4-thiomorpholinyl)-4-pyrimidinamine | (304) | | −52.0 |
| 126 | 1 HCl | A-1§,2§ | pure trans | N-cyclopropyl-2-(2-methylcyclopropyl)-6-(4-thiomorpholinyl)-4-pyrimidinamine | (290) | | +66.9 |
| 127 | 1 HCl | B-1§,2§ | pure trans | N-cyclopropyl-2-(2-methylcyclopropyl)-6-(4-thiomorpholinyl)-4-pyrimidinamine | (290) | | −68.6 |
| 128 | 1 maleate | achiral | | $N^4$-benzyl-$N^6$,2-dicyclopropyl-5-methyl-4,6-pyrimidinediamine | 295 | | |
| 129 | 1 maleate | achiral | | $N^4$-benzyl-$N^6$,2-dicyclopropyl-$N^4$,5-dimethyl-4,6-pyrimidinediamine | 309 | 74.5 | |
| 130 | 1 HBr | A-1,2 | rac trans | $N^4$-benzyl-$N^6$-cyclopropyl-2-(2-methylcyclopropyl)-4,6-pyrimidineamine | (294) | | |
| 131 | 1 maleate | achiral | | $N^4$,2-dicyclopropyl-5-methyl-$N^6$-[2-(methylsulfanyl)benzyl]-4,6-pyrimidinediamine | 341 | 132.7 | |
| 132 | 1 maleate | achiral | | $N^4$,2-dicyclopropyl-$N^6$-(2,6-difluorobenzyl)-5-methyl-4,6-pyrimidinediamine | 331 | 162.7 | |
| 133 | 1 maleate | achiral | | $N^4$,2-dicyclopropyl-$N^6$-(2-fluorobenzyl)-5-methyl-4,6-pyrimidinediamine | 313 | 141.9 | |
| 134 | 1 HCl | A-1,2 | rac trans | $N^4$-cyclopropyl-$N^6$-methyl-2-(2-methylcyclopropyl)-$N^6$-(2-nitrobenzyl)-4,6-pyrimidinediamine | 354 | | |
| 135 | 1 maleate | achiral | | $N^4$-[3,5-bis(trifluoromethyl)benzyl]-$N^6$,2-dicyclopropyl-5-methyl-4,6-pyrimidinediamine | 431 | 170.8 | |
| 136 | 1 maleate | achiral | | $N^4$,2-dicyclopropyl-$N^6$-(3,5-difluorobenzyl)-5-methyl-4,6-pyrimidinediamine | 331 | 184.9 | |
| 137 | 1 maleate | achiral | | $N^4$-cycloheptyl-$N^6$,2-dicyclopropyl-5-methyl-4,6-pyrimidinediamine | 301 | 136.1 | |
| 138 | 1 maleate | A-1,2 | rac trans | $N^4$-cycloheptyl-$N^6$-cyclopropyl-2-(2-methylcyclopropyl)-4,6-pyrimidinediamine | 301 | | |
| 139 | 1 maleate | achiral | | $N^4$-cyclohexyl-$N^6$,2-dicyclopropyl-$N^4$,5-dimethyl-4,6 pyrimidinediamine | 301 | (136-137) | |
| 140 | 1 maleate | achiral | | 5-chloro-$N^4$-cyclohexyl-$N^6$,2-dicyclopropyl-4,6-pyrimidinediamine | 307/309 | 62.9 | |
| 141 | 1 maleate | achiral | | $N^4$-cyclohexyl-$N^6$,2-dicyclopropyl-5-methyl-4,6-pyrimidinediamine | 287 | 159.7 | |
| 142 | 1 maleate | A-1,2 | rac trans | $N^4$-cyclohexyl-$N^6$-cyclopropyl-2-(2-methylcyclopropyl)-4,6-pyrimidinediamine | 287 | 174.3 | |
| 143 | | A-1§,2§ | pure trans | $N^4$-cyclohexyl-$N^6$-cyclopropyl-2-(2-methylcyclopropyl)-4,6-pyrimidinediamine | 287 | | 65.25 |
| 144 | | B-1§,2§ | pure trans | $N^4$-cyclohexyl-$N^6$-cyclopropyl-2-(2-methylcyclopropyl)-4,6-pyrimidinediamine | 287 | | −54.4 |
| 145 | 1 maleate | | mixt cis & trans | $N^4$,2-dicyclopropyl-5-methyl-$N^6$-(4-methylcyclohexyl)-4,6-pyrimidinediamine | 301 | 166.0 | |
| 146 | | A | pure cis or trans | $N^4$,2-dicyclopropyl-5-methyl-$N^6$-(4-methylcyclohexyl)-4,6-pyrimidinediamine | 301 | | |
| 147 | | achiral | | 1-[2-cyclopropyl-6-(cyclopropylamino)-5-methylpyrimidin-4-yl]azepan-2-one | 301 | | |
| 148 | 1 maleate | achiral | | N,2-dicyclopropyl-6-(3,4-dihydro-2(1H)-isoquinolinyl)-5-methyl-4-pyrimidinamine | 321 | 196.0 | |
| 149 | | achiral | | N,2-dicyclopropyl-6-(1,4-dioxa-8-azaspiro[4.5]dec-8-yl)-5-methyl-4-pyrimidinamine | 331 | 111.0 | |

TABLE 5-continued

| | Salt/solvate | Configuration data | | | Free base IUPAC NAME | MH+ (M+·) | DSC ° C. (mp) | alphaD |
|---|---|---|---|---|---|---|---|---|
| 150 | 1 maleate | | achiral | | N4,2-dicyclopropyl-N6-(2,2-diphenylethyl)-5-methyl-4,6-pyrimidinediamine | 385 | 157.4 | |
| 151 | 1 maleate | 1, 5 | mixt | | N,2-dicyclopropyl-5-methyl-6-(1,3,3-trimethyl-6-azabicyclo[3.2.1]oct-6-yl)-4-pyrimidinamine | 341 | | |
| 152 | 1 maleate | A-4a,8a | rac | trans | N,2-dicyclopropyl-5-methyl-6-octahydro-2(1H)-isoquinolinyl-4-pyrimidinamine | 327 | | |
| 153 | 1 HCl | | achiral | | 6-(8-azaspiro[4.5]dec-8-yl)-N,2-dicyclopropyl-5-methyl-4-pyrimidinamine | 327 | | |
| 154 | 1 maleate | | achiral | | 6-(1-azepanyl)-2-cyclopentyl-N-cyclopropyl-5-methyl-4-pyrimidinamine | 315 | | |
| 155 | | | achiral | | 4-azepan-1-yl-2-cyclopropyl-5,6,7,8-tetrahydro-pyrido[2,3-d]pyrimidine | 273 | | |
| 156 | | | achiral | | 4-azepan-1-yl-2-cyclopropyl-6,7,8,9-tetrahydro-pyrimido[4,5-b]azepine | 287 | | |
| 157 | | | achiral | | 4-azepan-1-yl-2-cyclopropyl-6,7-dihydro-pyrrolo[2,3-d]pyrimidine | | | |
| 172 | 1 fumarate | 1R, 2R & 1S, 2S | rac | trans | 6-(1-azepanyl)-2-cyclopropyl-5-methyl-N-(2-methylcyclopropyl)-4-pyrimidinamine | 301 | 138.0 | |
| 173 | 1 maleate | 1, 2 | rac | trans | {1-[6-(cyclopropylamino)-2-(2-methylcyclopropyl)-4-pyrimidinyl]-4-piperidinyl}methanol | 303 | 127.6 | |
| 174 | 1,5 fumarate | | achiral | | 6-(1-azepanyl)-2-cyclopropyl-5-methyl-N-(1-methylcyclopropyl)-4-pyrimidinamine | 301 | | |
| 175 | 1 maleate | | achiral | | N,2-dicyclopropyl-5-methyl-6-(1-piperidinyl)-4-pyrimidinamine | 273 | 110.1 | |
| 176 | 1 maleate | | achiral | | 6-(3-azabicyclo[3.2.2]non-3-yl)-N,2-dicyclopropyl-5-methyl-4-pyrimidinamine | 313 | | |
| 177 | 1 fumarate | 2 | rac | | N,2-dicyclopropyl-5-methyl-6-(2-methyl-1-piperidinyl)-4-pyrimidinamine | 287 | 186.3 | |
| 178 | | | achiral | | N4,2-dicyclopropyl-N6-(4-fluorobenzyl)-5-methyl-4,6-pyrimidinediamine | 313 | | |
| 179 | | | achiral | | N4,2-dicyclopropyl-5-methyl-N6-(2-methylbenzyl)-4,6-pyrimidinediamine | 309 | | |
| 180 | | | achiral | | N,2-dicyclopropyl-5-methyl-6-(1-pyrrolidinyl)-4-pyrimidinamine | 259 | | |
| 181 | 1 fumarate | 1R, 2S & 1S, 2R | rac | trans | 6-(1-azepanyl)-2-cyclopropyl-5-methyl-N-(2-phenylcyclopropyl)-4-pyrimidinamine | 363 | 156.2 | |
| 182 | | | achiral | | 1-[6-(3-bromoazetidin-1-yl)-2-cyclopropyl-5-methylpyrimidin-4-yl]azepane | 365/367 | 88.0 | |
| 183 | | | achiral | | 1-(6-azepan-1-yl-2-cyclopropyl-5-methylpyrimidin-4-yl)azetidine-3-carbonitrile | 312 | | |
| 184 | 1 maleate | | achiral | | 1-(6-azetidin-1-yl-2-cyclopropyl-5-methylpyrimidin-4-yl)azepane | 287 | 102.6 | |
| 185 | | | achiral | | 1-[2-cyclopropyl-5-methyl-6-(3-methylazetidin-1-yl)pyrimidin-4-yl]azepane | 301 | | |
| 186 | 1.5 fumarate | | achiral | | 1-[2-cyclopropyl-5-methyl-6-(3-methylazetidin-1-yl)pyrimidin-4-yl]azepane | 301 | 96.5 | |
| 187 | 2 fumarate | | achiral | | 1-[2-cyclopropyl-5-methyl-6-(3-methylazetidin-1-yl)pyrimidin-4-yl]azepane | 301 | 102.2 | |
| 188 | | | achiral | | 1-[2-cyclopropyl-6-(3,3-dimethylazetidin-1-yl)-5-methylpyrimidin-4-yl]azepane | 315 | | |
| 189 | 1 maleate | | achiral | | 1-(6-azepan-1-yl-2-cyclopropyl-5-methylpyrimidin-4-yl)azetidin-3-ol | 303 | 137.7 | |
| 190 | | | achiral | | 1-(6-azepan-1-yl-2-cyclopropyl-5-methylpyrimidin-4-yl)azetidin-3-yl methanesulfonate | 381 | 100.4 | |
| 191 | 1 fumarate | | achiral | | 1-[2-cyclopropyl-6-(3-methylazetidin-1-yl)pyrimidin-4-yl]azepane | 287 | 159.1 | |
| 192 | | | achiral | | 1-(6-azetidin-1-yl-2-cyclopropylpyrimidin-4-yl)azepane | 273 | 77.5 | |
| 193 | 1 H2O | | achiral | | 1-(6-azepan-1-yl-2-cyclopropyl-5-methylpyrimidin-4-yl)azetidin-3-one | 319 | | |
| 194 | | | achiral | | 1-[2-cyclopropyl-6-(3-fluoroazetidin-1-yl)-5-methylpyrimidin-4-yl]azepane | 305 | | |
| 195 | 1.5 fumarate | | achiral | | 1-[2-cyclopropyl-6-(3-fluoroazetidin-1-yl)pyrimidin-4-yl]azepane | 291 | 129.9 | |
| 196 | 1 maleate | | achiral | | 1-[2-cyclopropyl-6-(3-methoxyazetidin-1-yl)-5-methylpyrimidin-4-yl]azepane | 317 | | |

Compound 97 was resolved into its enantiomers by chromatography on a chiral support (Chiralpak AD Daicel, isopropanol/isohexane/diethylamine 5/95/0.1 (v/v), 30° C.) to give compound 99 (first eluted) and compound 100 (second eluted).
Compound 65 was resolved into its enantiomers by chromatography on a chiral support (Chiralpak AD Daicel, isopropanol/isohexane/diethylamine 5/95/0.1, 30° C.) to give compound 67 (second eluted) and compound 68 (first eluted).
Compound 142 was resolved into its enantiomers by chromatography on a chiral support (Chiralpak AD Daicel, isopropanol/isohexane/diethylamine 3/97/0.1, 30° C.) to give compound 143 (first eluted) and compound 144 (second eluted).
Compound 101 was resolved into its enantiomers by chromatography on a chiral support (Chiralpak AD Daicel, isopropanol/hexane mixture 4/96, 30° C.) to give compound 104 (first eluted) and compound 105 (second eluted).

EXAMPLE 8

Affinity for Human Muscarinic Receptors

Chinese Hamster Ovarian cells (CHO) expressing the human recombinant m1, m2, m3, m4 and m5 receptors were cultured in Ham's F12 media supplemented with 100 IU/ml of penicillin, 100 µg/ml of streptomycin, 400 µg/ml of geneticin and 5% of fetal bovine serum. Cell cultures were maintained in a humidified incubator at 37° C. and 5% $CO_2$.

Confluent CHO cells expressing human m1, m2, m3, m4 and m5 muscarinic receptors were harvested and resuspended in phosphate buffered saline without calcium and magnesium. The cell suspension was centrifuged at 1500×g for 3 min (4° C.). The cell pellet was homogenized in a 15 mM Tris-HCl (pH 7.5) buffer containing 2 mM $MgCl_2$, 0.3 mM EDTA and 1 mM EGTA. The crude membrane fraction was collected by two consecutive centrifugation steps at 40,000×g for 25 min (4° C.). The final pellet was resuspended, at a protein concentration ranging from 2 to 6 mg/ml, in a 7.5 mM Tris-HCl (pH 7.5) buffer containing 12.5 mM $MgCl_2$, 0.3 mM EDTA, 1 mM EGTA and 250 mM sucrose and stored in liquid nitrogen.

Binding assays were performed according to procedure described in: Buckley N. J., Bonner T. I., Buckley C. M., Brann M. R., Mol. Pharmacol. (1989), 35, 469-476, but with slight modifications.

Briefly, 25 to 50 µg of membrane proteins were incubated at room temperature in 1 ml of a 50 mM Tris-HCl (pH 7.4) buffer containing 2 mM of $MgCl_2$, 0.1 nM of [$^3$H]-NMS (N-methylscopolamine, 85 Ci/mmol, from Apbiotech, UK) and increasing concentrations of test compound dissolved in DMSO (1% final concentration). Non specific binding was measured in the presence of 1 µM atropine. After 60 (m2) or 120 (m3) min. incubation, assays were stopped by rapid vacuum filtration of the samples through glass fiber filters (Filtermat A, Wallac, Belgium) presoaked in 0.3% polyethyleneimine for at least 2 h. Samples were further rinsed with 8 ml of ice-cold 50 mM Tris-HCl (pH 7.4) buffer. Radioactivity trapped onto the filter was counted in a Betaplate counter (Wallac). Competition binding curves were analyzed by non-linear regression with XLfit software (UDBS, UK).

EXAMPLE 9

PDE IV Enzymatic Activity

Enzyme Source:

Cytosolic fraction from U937 cells pre-stimulated for 4 h at 37° C. with a mixture of rolipram 30 µM and salbutamol 1 µM (Torphy T. J., Zhou H. L., Cieslinski L. B., J. Pharmacol. Exp. Ther. (1992), 263 (3), 1195-1205).

SPA Phosphodiesterase Assay (Amersham Pharmacia Biotech; Belgium):

Assays were performed in 100 µL of 50 mM Tris HCl buffer (pH 7.4) containing 5 mM $MgCl_2$, 2 mM EGTA, 20 nM of [$^3$H]-cAMP (40-60 Ci/mmol), the cytosolic fraction of 50,000 U937 cells and the appropriate concentration of test compound (usually 10 µM) dissolved in DMSO (final assay concentration not exceeding 1%). After 30 min incubation at room temperature, 0.5 mg of SPA yttrium silicate beads are added to each sample. Radioactivity bound to the beads (5'-AMP) is determined by liquid scintillation. Non PDE IV activity and/or non specific binding of the labeled substrate to the SPA beads is defined as the residual radioactivity remaining in the presence of rolipram 32 µM (non PDE IV activity represents about 40% of total activity). PDE IV activity is determined by subtracting the non PDE TV activity from the total activity.

Compounds according to the invention showed $pIC_{50}$ values ranging from 6.5 to 10 for the m3 receptor, and showed $pIC_{50}$ values ranging from 5.7 to 8 for PDE IV. Dual high affinities were especially shown by compounds 55, 56, 57, 59, 60, 61, 62, 63, 64, 65, 66, 67, 72, 77, 78, 79, 80, 86, 87, 94, 95, 98, 106, 112, 115, 118, 119, 132, 144, 145, 154, 155, 156, 175, 176, 177, 180, 184, 185, 186, 187, 189, 191, 192 and 194.

EXAMPLE 10

In Vitro Inhibition of Carbachol-Induced Contraction of Guinea-Pig Trachea

The method was developed according to the procedure described in Leff P., Dougall I. G., Harper D., Br. J. Pharmacol. (1993), 110, 239-244. Tracheal rings were prepared from male Dunkin-Hartley guinea pig. Tissues were mounted in 20 ml organ baths containing modified Krebs' solution in the presence of $3.10^{-6}$ M indomethacin, $3.10^{-4}$ M hexamethonium and $10^{-6}$ M propranolol. The bathing solution was maintained at 37° C. and gassed with 95% $O_2$-5% $CO_2$. Tissues were allowed to equilibrate for a period of 60 min under a resting tension of 1 g. Isometric contractions were measured by force-displacement transducers coupled to an IOX computer system capable of controlling automatic data acquisition and bath washout by automatic fluid circulation through electrovalves at defined times. Drugs were manually or robotically injected into the bath according to the stability of the measured signal.

At the end of the 60 min period of stabilisation, the tracheas were contracted twice with $10^{-6}$ M carbachol at 30 min intervals. Two cumulative concentration-response curves were successively constructed in the absence or presence of the test compound (incubation time: 1 hour). Results were obtained from at least 3 or 4 individual experiments. Control tissues were treated with the solvent.

Antagonistic potency of the test compound was estimated by the calculation of $pD'_2$ and/or $pA_2$ values according to the methods described by Van Rossum (Van Rossum J. M., Hurkmans J. A. T. M., Wolters C. J. J., Arch. Int. Pharmacodyn. Ther. (1963), 143, 299-330) or Arunlakshana & Schild (Arunlakshana O., Schild H. O., Br. J. Pharmacol. (1959), 14, 48-58).

Preferred compounds according to the invention show $pA_2$ values typically ranging from 5.5 to 8.

The invention claimed is:

1. A compound having the formula I, or a pharmaceutically acceptable salt thereof,

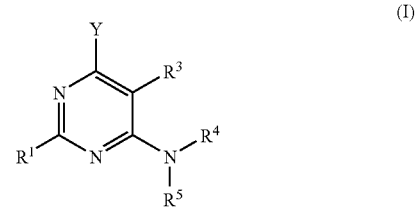

wherein
Y is —NH—R² or a group of formula

R¹ is cycloalkyl or non-substituted alkyl,
R² is cycloalkyl,
R³ is hydrogen, alkyl, halogen, hydroxy, alkoxy or amino,
Rᵃ is hydrogen, alkyl, alkenyl, alkynyl, halogen, hydroxy, alkoxy, amino, alkylamino, alkylsulfonyloxy, cyano, carboxy, ester or amido,
Rᵇ is hydrogen, alkyl or halogen,
or RᵃRᵇ is carbonyl,
R⁴ is hydrogen or alkyl,
R⁵ is cycloalkyl, arylalkyl or heterocycle-alkyl,
or NR⁴R⁵ is a heterocycle, which may be substituted, containing only one heteroatom which is a nitrogen atom or containing two heteroatoms wherein one is a nitrogen atom and the other is a non-oxidized sulfur atom,
with the proviso that when Y is a group of formula

R¹ is a cycloalkyl.

2. A compound according to claim 1 wherein Y is —NH—R².

3. A compound according to claim 2 wherein
R¹ is C3-7-cycloalkyl or non-substituted alkyl,
R² is C3-7-cycloalkyl,
R³ is hydrogen, C1-4-alkyl, halogen, hydroxy, alkoxy or amino,
R⁴ is hydrogen or C1-4-alkyl,
R⁵ is C3-7-cycloalkyl, arylalkyl or heterocycle-alkyl,
or NR⁴R⁵ is a heterocycle, which may be substituted, containing only one heteroatom which is a nitrogen atom or containing two heteroatoms wherein one is a nitrogen atom and the other is a non-oxidized sulfur atom.

4. A compound according to claim 2 wherein R¹ is C3-4-alkyl or C3-5-cycloalkyl.

5. A compound according to claim 2 wherein
R² is a C3-4-non-substituted cycloalkyl, or a cycloalkyl substituted by a C1-6-alkyl or an aryl,
and/or R³ is hydrogen, methyl, ethyl, a Cl atom, a F atom, a Br atom, amino or methoxy.

6. A compound according to claim 2 wherein
R⁴ is hydrogen or C1-4-alkyl,
and/or R⁵ is 2-(2-thienyl)ethyl, 2-furylmethyl, 2-thienylmethyl, 4-pyridinylmethyl, benzyl, 2-(methylsulfanyl)benzyl, 2,6-difluorobenzyl, 2-fluorobenzyl, 2-nitrobenzyl, 3,5-bis(trifluoromethyl)benzyl, 3,5-difluorobenzyl, cyclohexyl, cycloheptyl, 4-methylcyclohexyl, or 2,2-diphenylethyl,
or NR⁴R⁵ is 1,3-thiazolidin-3-yl, 1-azepanyl, 1-azocanyl, 3,5-dimethyl-1-piperidinyl, 4-(2-methoxyphenyl)-1-piperidinyl, 4-(hydroxy(diphenyl)methyl)-1-piperidinyl, 4-(trifluoromethyl)-1-piperidinyl, 4,4-difluoro-1-piperidinyl, 4,4-dimethyl-1-piperidinyl, 4-carbamoyl-1-piperidinyl, 4-benzyl-1-piperidinyl, 4-carboxy-1-piperidinyl, 4-cyano-4-phenyl-1-piperidinyl, 4-ethoxycarbonyl-1-piperidinyl, 4-ethyl-1-piperidinyl, 4-ethyl-4-methyl-1-piperidinyl, 4-hydroxy-1-piperidinyl, 4-hydroxy-4-phenyl-1-piperidinyl, 4-hydroxymethyl-1-piperidinyl, 4-methyl-1-piperidinyl, 4-methylene-1-piperidinyl, 4-oxo-1-piperidinyl, 3,6-dihydro-1(2H)-pyridinyl, 3-azabicyclo[3.2.1]oct-3-yl, 4-thiomorpholinyl, 2-one-1-azepanyl, 3,4-dihydro-2(1H)-isoquinolinyl, 1,4-dioxa-8-azaspiro[4.5]dec-8-yl, 1,3,3-trimethyl-6-azabicyclo[3.2.1]oct-6-yl, octahydro-2(1H)-isoquinolinyl or 8-azaspiro[4.5]dec-8-yl.

7. A compound selected from
6-(1-azepanyl)-N,2-dicyclopropyl-5-methyl-4-pyrimidinamine;
N,2-dicyclopropyl-6-(4,4-dimethyl-1-piperidinyl)-5-methyl-4-pyrimidin-amine;
N,2-dicyclopropyl-5-methyl-6-(4-methyl-1-piperidinyl)-4-pyrimidinamine;
6-(3-azabicyclo[3.2.1]oct-3-yl)-N,2-dicyclopropyl-5-methyl-4-pyrimidinamine;
N,2-dicyclo-propyl-5-methyl-6-(4-thiomorpholinyl)-4-pyrimidinamine; and
pharmaceutically acceptable salts thereof.

8. A compound according to claim 1 wherein Y is a group of formula

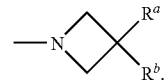

9. A compound according to claim 8 wherein NR⁴R⁵ is a 5- to 9-membered heterocycle, which may be substituted, containing only one heteroatom which is a nitrogen atom or containing two heteroatoms wherein one is a nitrogen atom and the other is a non-oxidized sulfur atom.

10. A compound according to claim 9 wherein
R¹ is C3-7-cycloalkyl,
R³ is hydrogen, C1-4-alkyl, halogen, hydroxy, alkoxy or amino,
Rᵃ is hydrogen, C1-4-alkyl, C2-6-alkenyl, C2-6-alkynyl, halogen, hydroxy, alkoxy, amino, alkylamino, alkylsulfonyloxy, cyano, carboxy, ester or amido,
Rᵇ is hydrogen, C1-4-alkyl or halogen,
or RᵃRᵇ is carbonyl.

11. A compound according to claim 10 wherein R¹ is C3-4-cycloalkyl.

12. A compound according to claim 10 wherein R³ is hydrogen or C1-4-alkyl.

13. A compound according to claim 10 wherein
Rᵃ is hydrogen, methyl, hydroxy, methoxy, methylsulfonyloxy, a Br atom, a F atom or cyano,
and/or Rᵇ is hydrogen or methyl,
or RᵃRᵇ is carbonyl.

14. A compound selected from
1-(6-azetidin-1-yl-2-cyclopropyl-5-methylpyrimidin-4-yl)azepane;
1-[2-cyclopropyl-5-methyl-6-(3-methylazetidin-1-yl)pyrimidin-4-yl]azepane; and
pharmaceutically acceptable salts thereof.

15. A compound according to claim 1 as a pure enantiomer.
16. A compound according to claim 7 as a pure enantiomer.
17. A compound according to claim 14 as a pure enantiomer.
18. A compound according to claim 4 wherein R¹ is cyclopropyl, isopropyl, cyclobutyl, cyclopentyl, 2-methyl-cyclopropyl or cyclopropylmethyl.

19. A compound according to claim 5 wherein $R^2$ is cyclopropyl or cyclobutyl.

20. A compound according to claim 6 wherein $R^4$ is hydrogen or methyl.

21. A compound according to claim 9 wherein $NR^4R^5$ is 1-azepanyl, which may be substituted.

22. A compound according to claim 11 wherein $R^1$ is cyclopropyl.

23. A compound according to claim 12 wherein $R^1$ is hydrogen or methyl.

24. A compound according to claim 13 wherein $R^a$ is hydrogen, methyl, hydroxy or a F atom, and/or $R^b$ is hydrogen.

25. A pharmaceutical composition comprising an effective amount of a compound according to claim 1 in combination with a pharmaceutically acceptable diluent or carrier.

26. A pharmaceutical composition according to claim 25 for administration by inhalation.

27. A pharmaceutical composition comprising an effective amount of a compound according to claim 7 in combination with a pharmaceutically acceptable diluent or carrier.

28. A pharmaceutical composition comprising an effective amount of a compound according to claim 14 in combination with a pharmaceutically acceptable diluent or carrier.

29. A pharmaceutical composition according to claim 27 for administration by inhalation.

30. A pharmaceutical composition according to claim 28 for administration by inhalation.

31. A method for treating Chronic Obstructive Pulmonary Disease comprising administering a therapeutically effective amount of at least one compound according to claim 1 or a pharmaceutically acceptable salt thereof to a patient.

32. A method for treating Chronic Obstructive Pulmonary Disease comprising administering a therapeutically effective amount of at least one compound according to claim 7 or a pharmaceutically acceptable salt thereof to a patient.

33. A method for treating Chronic Obstructive Pulmonary Disease comprising administering a therapeutically effective amount of at least one compound according to claim 14 or a pharmaceutically acceptable salt thereof to a patient.

* * * * *